United States Patent
Brown et al.

(10) Patent No.: US 6,702,719 B1
(45) Date of Patent: Mar. 9, 2004

(54) EXERCISE MACHINE

(75) Inventors: Michael Wayne Brown, Georgetown, TX (US); Kelvin Roderick Lawrence, Round Rock, TX (US); Michael A. Paolini, Round Rock, TX (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/561,422

(22) Filed: Apr. 28, 2000

(51) Int. Cl.$^7$ .............................................. A63B 22/00
(52) U.S. Cl. .................... 482/8; 482/9; 482/4
(58) Field of Search .................... 482/1–9, 900–902

(56) References Cited

U.S. PATENT DOCUMENTS

| | | | |
|---|---|---|---|
| 4,817,940 A | 4/1989 | Shaw et al. | |
| 4,828,257 A | 5/1989 | Dyer et al. | |
| 4,891,785 A | 1/1990 | Donohoo | |
| 5,204,670 A | 4/1993 | Stinton | |
| 5,213,555 A | 5/1993 | Hood et al. | |
| 5,335,188 A | 8/1994 | Brisson | |
| 5,387,164 A | 2/1995 | Brown, Jr. | |
| 5,435,799 A | 7/1995 | Lundin | |
| 5,598,849 A | 2/1997 | Browne | |
| 5,702,323 A | 12/1997 | Poulton | |
| 5,785,632 A | 7/1998 | Greenberg et al. | |
| 5,799,281 A | 8/1998 | Login et al. | |
| 5,816,443 A | 10/1998 | Bustos | |
| 5,888,172 A | 3/1999 | Andrus et al. | |
| 5,937,387 A | 8/1999 | Summerell et al. | |
| 5,957,699 A | 9/1999 | Peterson et al. | |
| 5,973,696 A | 10/1999 | Agranat et al. | |
| 5,976,083 A | 11/1999 | Richardson et al. | |
| 5,984,839 A | 11/1999 | Corkum | |
| 6,042,519 A | 3/2000 | Shea | |
| 6,053,844 A | * 4/2000 | Clem | 482/8 |
| 6,193,631 B1 | * 2/2001 | Hickman | 482/8 |
| 6,464,618 B1 | 10/2002 | Shea | |

* cited by examiner

*Primary Examiner*—Glenn E. Richman
(74) *Attorney, Agent, or Firm*—Marilyn Smith Dawkins; Bracewell & Patterson, L.L.P.

(57) ABSTRACT

In accordance with the present invention, an exercise machine receives exercise-related data for a particular user via a communication interface with an independent computing device specified by the particular user, such as a portable computer system, personal storage device, or network system. The exercise machine specifies control of the exercise machine according to the exercise-related data for the particular user, such that a particular level of control of the exercise machine is specified according to exercise-related data for the particular user from the independent computing device. In addition, the exercise machine transmits indicators of usage of the exercise machine to a server system that may be utilized by a manufacturer to track the usage of a particular exercise machine.

14 Claims, 5 Drawing Sheets

EXERCISE MACHINE

CROSS-REFERENCE TO RELATED APPLICATIONS

The present application is related to the following co-pending applications, which are filed on even date herewith and incorporated herein by reference:

(1) U.S. patent application Ser. No. 09/561,130
(2) U.S. patent application Ser. No. 09/561,426
(3) U.S. patent application Ser. No. 09/561,115
(4) U.S. patent application Ser. No. 09/561,134

BACKGROUND OF THE INVENTION

1. Technical Field

The present invention relates to an improved exercise machine in general and, in particular, to an improved method, system and program for controlling an exercise machine. Still more particularly, the present invention relates to a method, system and program for controlling an exercise machine via control signals received from multiple types of computing devices that are independent of any one exercise machine, but may be utilized interactively with the exercise machine intended for use by a particular user.

2. Description of the Prior Art

A fitness craze has recently swept the United States and other countries. From fat-free potato chips to treadmills, people around the world have become obsessed with weight loss and healthy living. Accordingly, record numbers of new fitness products/exercise equipment from multiple manufacturers have emerged to meet this obsession (including stair climbers, treadmills, recumbent bicycles, ski machines, rowing machines, weight lifting machines, and the like).

Many pieces of exercise equipment, when utilized regularly, are very useful for weight loss, for improving cardiovascular stamina, and for strengthening various muscles. Most exercise equipment includes a monitoring device that may include a pulse monitor, a distance meter, a rate monitor, a time monitor, a strain gauge, an accelerometer and/or any other sensor for measuring the physical activity/performance level of an user on the equipment. Moreover, monitoring devices typically request personal data from the user such as age, weight and desired physical fitness level. The monitoring device utilizes the personal data in combination with physical exertion and heart rate to estimate calories burned, fitness levels met, and other fitness related data. In addition, the monitor may adjust the resistance or speed of a piece of exercise equipment in order to aid the user in reaching and/or maintaining a fitness level for that exercise session.

One limiting factor of many exercise machines and monitors is that the user must reenter their personal data to the monitor each time the user utilizes an exercise machine. In addition, most exercise machines do not have a previous history of the user from which to provide data about improvement and to provide additional fitness goals. However, one solution to providing a history for a user is provided in U.S. Pat. No. 5,335,188 ('188). In '188, a speed and time elapsed of an exercise session on a bicycle is recorded. The user may choose to save the speed and time of an exercise session under an identifier for the user. The user may later select a particular exercise session as a standard of performance for subsequent performances whereby each subsequent performance is compared with the selected exercise session. However, while the bicycle monitor memory stores exercise sessions for a particular user at that bicycle, in a club or other venue where multiple bicycles are provided, the user may not always have access to the bicycle at which the session data is stored in order to add to the data.

Another limiting factor of many exercise machines is that they operate and monitor the user independent of one another. However, cross-training across multiple machines is popular in order to exercise different parts of the body. An individual may spend 20 minutes on a treadmill working a hills program where the monitor for the treadmill calculates a certain number of calories burned and other fitness related data. The individual may then move to a rowing machine that does not realize that the user has already worked for 20 minutes and thus calculates calories burned and other fitness related data as if the user only worked out on the rowing machine. An overall fitness level achieved by the user after working on both machines is not provided.

One solution to cross-training across multiple machines is provided in U.S. Pat. No. 5,598,849 ('849). In '849, an individual is provided with a user monitor that has a preferred exercise regimen of physical parameters such as heart rate stored therein. The user is required to monitor at least one physical parameter with the assistance of the user monitor and is preferably required during exercise to control his exercise to maintain the physical parameter as closely as possible to the preset values. After exercising is completed, the monitored physical parameters are proffered from the user monitor and sent to a master data processing system where the monitored parameters are stored and compared with the preset parameters in order to develop a fitness profile. However, a real-time fitness profile is not provided by the prior art. In addition, the exercise regimen is not alterable during the workout. Moreover, the user monitor is limited in that it operates independent of the exercise machine and therefore does not provide feedback to the exercise machine in order that resistance or another variable may be adjusted.

Moreover, another limiting factor of many exercise machines is that they are boring to utilize because of their inability to encourage a user to continue exercising. Display screens that depict a user's location within a selected exercise program may be provided; however, they typically include dull graphics. one solution to improving graphical rendering is provided in U.S. Pat. No. 5,947,868 ('868). In the '868 patent, an exercise monitor outputs a signal representative of the performance level of a user utilizing the exercise equipment (e.g. pulse rate, distance traveled, time exercised, rate of exercise, etc.). The performance level signal then is fed to a video game player wirelessly or via a cable.

The video game player preferably utilizes a hand-held video game player. To simulate the user, the output from the exercise monitor is utilized to control the video game character's performance level within a video game that runs on the video game player. For example, the lifetime of a video game character may be increased by peddling faster. However, while the video game player provides a graphical venue by which the user controls a video game character according to their fitness level, other types of graphical rendering, other than a video game are not provided. In addition, in order to utilize the video game player, a monitor that supplies a particular type of performance level signal must be coupled to the exercise machine. Another limiting factor of many exercise machines is that they do not provide a display that is adjustable dependent upon the user. For example, existing systems are limited in that they do not offer displaying output from an exercise machine in a particular language, dependent upon the user.

Yet another limiting factor of exercise machines is that the actual usage of exercise machines is typically not trackable by an exercise machine manufacturer. In addition, exercise machines are limited because in order to purchase an upgrade for an exercise machine, one is typically required to purchase an entirely new apparatus, which can be costly.

Therefore, in view of the aforementioned, it would be advantageous to provide an exercise machine that is enabled to receive personal data, fitness goals and/or control signals for a particular user from multiple types of data storage media and computing devices that are independent of any one exercise machine. In particular, it would be advantageous to receive such data from a data storage media that is enabled to be utilized interactively with any one exercise machine while the particular user is exercising. In addition, it would be advantageous to provide for an exercise machine to support removable output interfaces such that the particular user can provide the type of output interface desired. Moreover, it would be advantageous to provide an exercise machine that may broadcast current usage information to a manufacturer and may receive upgrades from a manufacturer.

SUMMARY OF THE INVENTION

In view of the foregoing, it is therefore an object of the present invention to provide an improved exercise machine.

It is another object of the present invention to provide an improved method, system and program for controlling an exercise machine.

It is yet another object of the present invention to provide an improved method, system and program for controlling an exercise machine via control signals received from multiple types of computing devices that are independent of any one exercise machine, but may be utilized interactively with the exercise machine intended for use by a particular user.

In accordance with the present invention, an exercise machine receives exercise-related data for a particular user via a communication interface with an independent computing device specified by the particular user, such as a portable computer system, personal storage device, or network system. The exercise machine specifies control of the exercise machine according to the exercise-related data for the particular user, such that a particular level of control of the exercise machine is specified according to exercise-related data for the particular user from the independent computing device. In addition, the exercise machine transmits indicators of usage of the exercise machine to a server system that may be utilized by a manufacturer to track the usage of a particular exercise machine.

All objects, features, and advantages of the present invention will become apparent in the following detailed written description.

DESCRIPTION OF THE DRAWINGS

The invention itself as will as a preferred mode of use, further objects, and advantages thereof, will best be understood by reference to the following detailed description of an illustrative embodiment when read in conjunction with the accompanying drawings, wherein.

DESCRIPTION OF A PREFERRED EMBODIMENT

The present invention may be executed in a variety of systems, including a variety of computing systems and electronic devices under a number of different operating systems. In a preferred embodiment of the present invention, the computer system is a portable computing system such as a notebook computer, a palmtop computer, a personal digital assistant, a telephone or other electronic computing system that may also incorporate communication features that provide for telephony, enhanced telephony, messaging and information services. However, the computer system may also be, for example, a desktop computer, a network computer, a midrange computer or a mainframe computer. Preferably, in order to enable at least one of these communication features, the computer system is able to be connected to a network, such as the Internet by either a wired link or wireless link. In addition, the computer system may be a stand-alone system or part of a network such as a local-area network (LAN) or a wide-area network (WAN). Therefore, in general, the present invention is preferably executed in a computer system that performs computing tasks such as manipulating data in storage that is accessible to the computer system. In addition, the computer system includes at least one output device and at least one input device.

Figure 1:
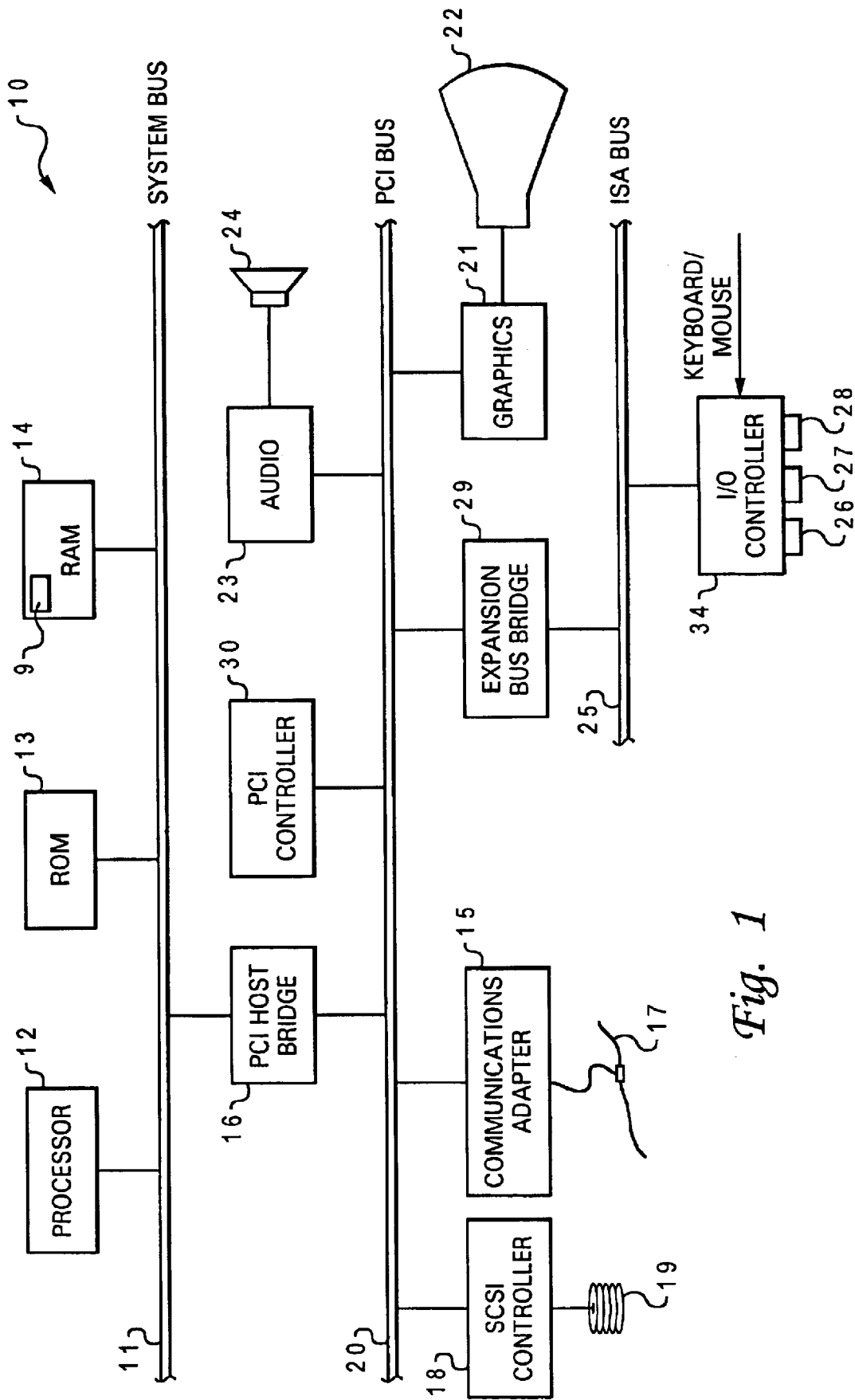
FIG. 1 depicts one embodiment of a data processing system with which the method, system and program of the present invention may advantageously be utilized.

Referring now to the drawings and in particular to FIG. 1, there is depicted a block diagram of one embodiment of a computer system that may utilize the present invention. As depicted, data processing system 10 includes at least one processor 12, which is coupled to system bus 11. Each processor 12 is a general-purpose processor, such as IBM's PowerPC™ processor that, during normal operation, processes data under the control of operating system and application software stored in random access memory (RAM) 14 and Read Only Memory (ROM) 13. The operating system preferably provides a graphical user interface (GUI) to the user. Application software contains instructions that when executed on processor 12 carry out the operations depicted in the flowcharts of FIG. 6 and others described herein.

Processors 12 are coupled via system bus 11 and Peripheral Component Interconnect (PCI) host bridge 16 to PCI local bus 20. PCI host bridge 16 provides a low latency path through which processor 12 may directly access PCI devices mapped anywhere within bus memory and/or I/O address spaces. PCI host bridge 16 also provides a high bandwidth path for allowing PCI devices to directly access RAM 14.

PCI local bus 20 interconnects a number of devices for communication under the control of PCI controller 30. These devices include a Small Computer System Interface (SCSI) controller 18, which provides an interface to SCSI hard disk 19, and communications adapter(s) 15, which interface data processing system 10 to at least one data communication network 17 comprising wired and/or wireless network communications. In addition, an audio adapter 23 is attached to PCI local bus 20 for controlling audio output through speaker 24. A graphics adapter 21 is also attached to PCI local bus 20 for controlling visual output through display monitor 22. In alternate embodiments of the present invention, additional peripheral components may be added. For example, in alternate embodiments, a tactile display component may be provided.

PCI local bus 20 is further coupled to an Industry Standard Architecture (ISA) bus 25 by an expansion bus bridge 29. As shown, ISA bus 25 has an attached I/O (Input/Output) controller 34 that interfaces data processing system 10 to peripheral input devices such as a keyboard and mouse (not illustrated) and supports external communication via parallel, serial and universal serial bus (USB) ports 26, 27, and 28, respectively.

Figure 2:
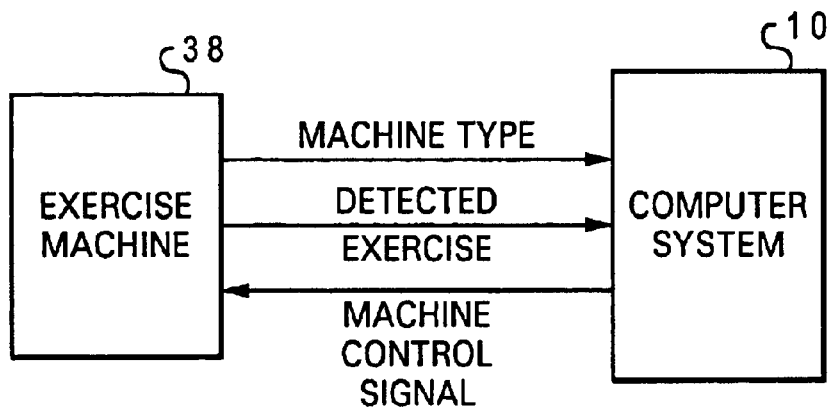
FIG. 2 illustrates a preferred embodiment of a system for controlling an exercise machine in accordance with the method, system and program of the present invention.

With reference now to FIG. 2, there is depicted one embodiment of a block diagram of a system for controlling an exercise machine in accordance with the method, system and program of the present invention.

Exercise machine platforms may represent any exercise machine that controls, for example, aerobic and strength results for a user during exercise. For example, an exercise machine 38 advantageously includes movable parts that provide a platform for a user to exert energy that can be measured. In addition, exercise machine platforms, such as exercise machine 38 advantageously allow for controlling the resistance, pressure, speed and other factors of the mechanized parts of the platform such that by utilizing exercise machine 38 to guide exercise, a user participates in controlled exercize movements. In particular, exercise machine 38 may include a selection of the components depicted for a computer system in FIG. 1.

Exercise machine 38 is advantageously enabled to communicate with multiple diverse types of data storage media and data processing systems, such as computer system 10 that is an independent computing device detectable by multiple diverse exercise machines, via a bi-directional communication medium. For example, a machine type of exercise machine 38, including a model number, may be transmitted from exercise machine 38 to computer system 10. In addition, an indicator of detected exercise may be transmitted from exercise machine 38 to computer system 10. Moreover, the movement of any parts controlled by exercise machine 38 may be controlled according to a machine control signal transmitted from computer system 10 to exercise machine 38 across the communications medium.

The bi-directional communications medium may include wired or wireless communications or other communications media that enables bi-directional transmission of data. Moreover, the communications medium may include a link to a network, such as the Internet, or a direct data link.

In a wired embodiment of the communications medium, for example, exercise machine 38 is connected to computer system 10 via parallel, serial, or USB ports, or the communication adapter as depicted in FIG. 1. In a wireless embodiment of the communications medium, for example, exercise machine 38 is wirelessly connected to computer system 10 via infrared, radio frequency (RF), cellular and other wireless transmissions that are detectable by computer system 10.

Data exchange across the communications medium is advantageously performed in at least one of multiple available data transmission protocols and is preferably supported by a common data structure format, such as the extensible mark-up language (XML) data structure format. Data transmission protocols may include, but are not limited to, Transmission Control Protocol (TCP), Internet Protocol (IP), Hypertext Transfer Protocol (HTTP), and Bluetooth. In addition, data may be transmitted in a secure manner via encryption or by technologies such as secure socket layer (SSL) or virtual private networks (VPN).

An example of an XML data file that might be transmitted to exercise machine 38, as depicted below, preferably contains data that is distinguished by attributes on elements and may be wrapped within a larger element. For example, the data attributed to element "<TimeStamp></TimeStamp>" designates the time that the data was attributed to the XML data file.

<TREADMILL TimeStamp="888965153"

MachineType="Arc2000" UserID="JANEXYZ" Speed="30"

Elevation="5">

In addition, in an alternate example, the XML data file might be formatted utilizing elements, as illustrated below.

<TimeStamp>888965153</TimeStamp>

<MachineType>Arc2000</MachineType>

<UserID>JANEXYZ</UserID>

<Speed>30</Speed>

<Elevation>5</Elevation>

In the example, as will be further described, exercise machine 38 would receive the example XML data file and utilize the XML data file to control operation of exercise machine 38. The above described XML data file example is intended as a functional example of an XML data file that would control the speed and elevation of a treadmill. The elements, format of the elements and data included with the elements is provided to depict an example and is not intended to limit the types of elements, format of elements or data included with elements that are in an XML data file.

In the example of the XML data format as the common transmittable data format, a data validation file such as a document type definition (DTD) or schema is preferably utilized to validate XML data files. In addition, a schema preferably translates multiple XML data files. Moreover, a style sheet such as an extensible stylesheet language (XSL) file is preferably utilized to provide a style specification for the XML data at the receiving system. In particular, DTDs, schemas, and XSL files may be, for example, transmitted with an XML data file to a receiving system or downloaded at the receiving system from an alternate source. In the present example, the DTD or schema would verify that all the data required for transmittal to a particular exercise machine is included in the XML data file. For example, a speed and elevation may be required to validate the XML data file.

Exercize machine 38 advantageously transmits measurements in the common transmittable data structure format from real-time monitoring systems associated with exercise machine 38 including, but not limited to, a pulse monitor, a distance meter, a rate monitor, a time monitor, a strain gauge, an accelerometer and/or any other sensor for measuring the physical activity/performance level of a user on a piece of equipment.

Detected exercise signals, such as a pulse, distance, rate, time, strain, etc, are preferably transmitted from exercise machine 38 in an XML data format. For example, an example of an XML data file for a pulse monitor is described below where a user's pulse is measured between a particular time period at 80 beats per minute. In addition, an alternate form of XML formatting may be utilized.

<TimeRange>888965153,888965160</TimeRange>

<MachineID>45365</MachineID>

<MachineType>PulseMonitor</MachineType>

<Rate>80</Rate>

Multi-machine detectable computer system 10 is advantageously a computer system that is independent of any one exercise machine and is detectable by multiple diverse types of exercise machines. For example, computer system 10 may be a portable computer system, such as a personal digital assistant (PDA), laptop computer system, or mobile telephone system as described in U.S. patent application Ser. No. 09/561,115, herein incorporated by reference. In addition, computer system 10 may include a server system that is accessible via a network as described in U.S. patent application Ser. No. 09/561,426, herein incorporated by reference. Moreover, portable computer system 10 may comprise a personal storage device, such as a smart card, with limited processing power, where a personal storage device adapter is coupled to exercise machine 38 in order to read the personal storage device, as described in U.S. patent application Ser. No. 09/561,130, herein incorporated by reference.

Computer system 10 may store multiple types of exercise related data for a particular user and perform multiple functions. For example, computer system 10 may compute current fitness activity for an exerciser from the detected exercise signal transmitted from exercise machine 38. Current fitness activity may be accumulated across multiple exercise machines during a particular exercise session or period of time. In computing current fitness activity, personal data for the user may be utilized by computer system 10 to specify the computations. Moreover, a user may advantageously input exercise performed independent of an exercise machine whereby computer system 10 updates current fitness activity and computer system 10 may be equipped with additional sensors to detect exercise parameters. Therefore, current fitness activity calculated by computer system 10 includes cumulative fitness activity performed by a user during a particular period of time, possibly across multiple exercise machines and/or independent of exercise machines, that is specified according to the user.

In addition, computer system 10 may include control programs for multiple types of exercise machines. As previously described, exercise machine 38 may receive a control program in a particular transmittable data format and utilize the control program to control movement of any parts. In particular, computer system 10 may include a schedule of exercise machines for the user to utilize and pre-selected control programs for automatic transmission to the scheduled exercise machines. Alternatively, when a machine type is detected by computer system 10, a selection of available control programs for the user to select from may be provided by computer system 10.

As previously described, computer system 10 may include personal data for a user and fitness goals for the user. For example, personal data may include the user's weight, height, age, percentage body fat, bone density, metabolism, health problems, prescriptions, diet, and other health related factors. Fitness goals may include the number of calories that the user wants to burn or the number of repetitions at a particular weight that the user needs to perform on a strength training apparatus.

As a user exercises, the detected exercise signals received from exercise machine 38 are preferably compared at computer system 10 with the goals of the exercise control program, the user's overall fitness goals, and personal data. For example, a heart rate of the user may be compared with a target heart rate for the control program in view of the length of time the user's heart rate has been at a particular level. If a user is not reaching target goals, an indicator may be output to the user and/or the machine control signal to exercise machine adjusted to facilitate the user reaching target goals. If the user is exceeding target goals, an indicator may be output to the user and/or the machine control signal adjusted to reduce exercise intensity.

Additionally, computer system 10 advantageously includes output preferences for a particular user. For example, a user may prefer to output data, such as current fitness activity, to an audio output, rather that a video output. In another example, a user may specify an output preference for a game or other graphical output application to output fitness activity data.

Computer system 10 is advantageously utilized as a personal exercise monitor for monitoring exercise across multiple diverse exercise machine platforms and a temporary controller for controlling movement of multiple diverse exercise machine platforms when in use by a user associated with computer system 10. It is important to note that a user is able to customize the features available on computer system 10. Since the user advantageously supplies computer system 10, the user may select the type and quality of desired output. For example, the user may download games, audio and other programs from signal-bearing media into data storage medium 51. In addition, the user may utilize a computer system that includes a color display, or alternatively a black and white display. In addition, it is important to note that computer system 10 may be continuously upgraded without requiring the upgrade of machine monitor 40.

Figure 3:
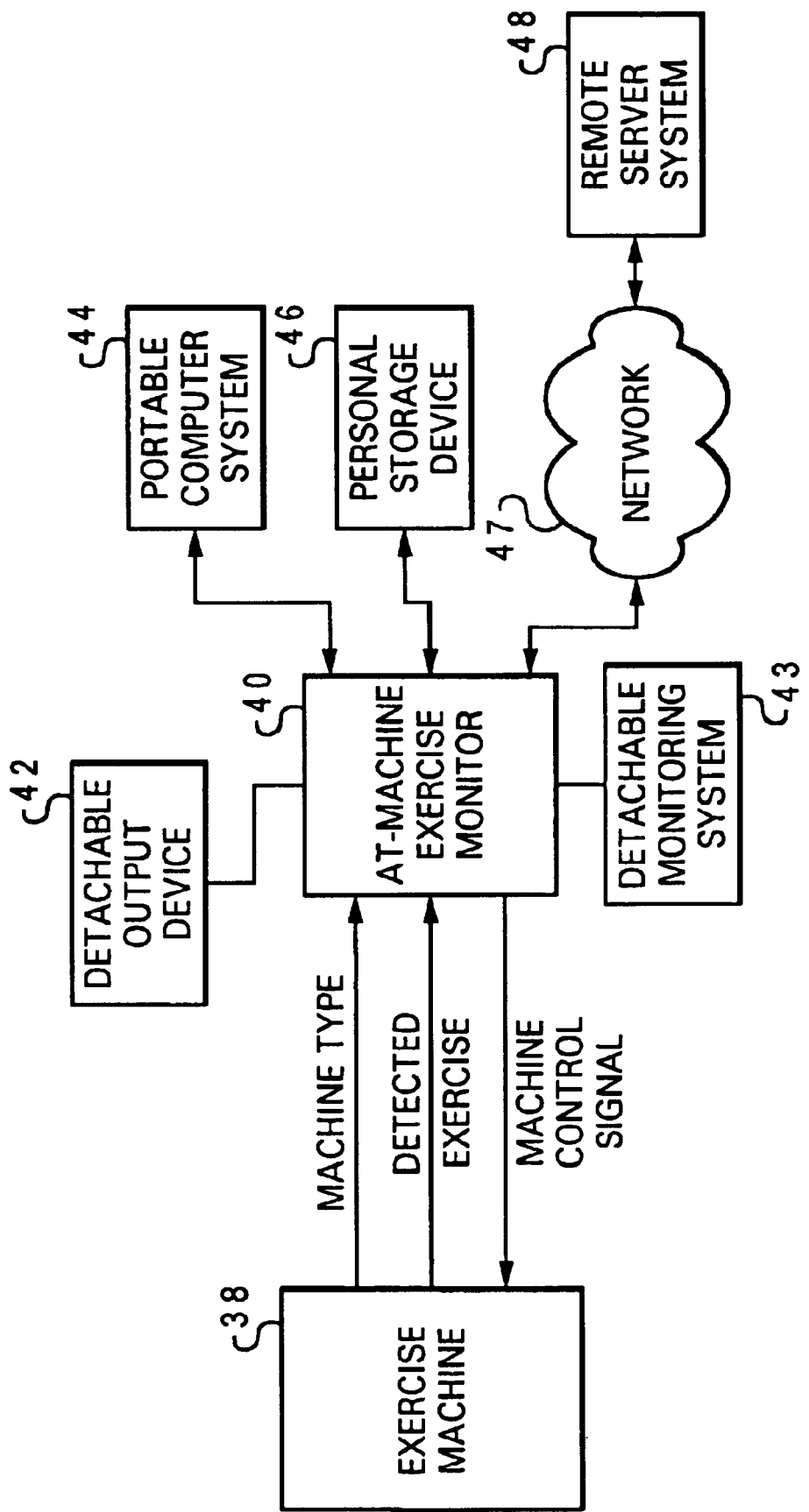
FIG. 3 depicts a second embodiment of a system for controlling an exercise machine in accordance with the method, system and program of the present invention.

With reference now to FIG. 3, there is depicted a second embodiment of a system for controlling an exercise machine in accordance with the method, system and program of the present invention. As depicted, an at-machine exercise monitor 40 is permanently coupled with exercise machine 38 via a communication medium. At-machine exercise monitor 40 is advantageously enabled to receive a machine type signal and detected exercise from exercise machine 38 and transmit the machine type signal and detected exercise to an alternate computer system. In addition, at-machine exercise monitor 40 is advantageously enabled to receive and/or determine a machine control signal and transmit the machine control signal to exercise machine 38.

For example, at-machine exercise monitor 40 may be temporarily coupled with independent computing devices including, but not limited to, a portable computer system 44, a personal storage device 46 or a remote server system 80 via a communication medium, wherein portable computer system 44, personal storage device 46 or remote server system 80 perform like computer system 10 of FIG. 2.

At-machine exercise monitor 40 is advantageously enabled to communicate with a network 47, such as the Internet, with remote server system 48. In particular, a user may enter a universal identifier associated with the user, such as a web page identifier, that is transmitted to network 47 in order to obtain access to a remote server system that is addressed by the web page identifier, such as remote server system 48. Remote server system 48 includes exercise-related data associated with the user of the universal identifier.

At-machine exercise monitor 40 is preferably enabled with at least one connector for a detachable output device 42. Detachable output device 42 may be provided by a user while the user is exercising at exercise machine 38 and is advantageously enabled across multiple is diverse types of exercise machines. In particular, output preferences for the type of output to detachable output device 42 may be received at at-machine exercise monitor 40 from any of the independent computing devices. In addition to output preferences received from the external computing devices, at-machine exercise monitor 40 may receive graphical output applications, such as video games, that are utilized to output data such as current fitness activity.

In addition to any real-time monitoring system coupled to exercise machine 38, exercise machine 38 is advantageously enabled with at least one connector for a user to provide additional monitoring systems, such as detachable monitoring system 43. Preferably, any additional monitoring systems are designed to transmit monitored data in the common data format utilized by exercize machine 38, for example XML. Exercise machine 38 is advantageously enabled to track and utilize additional types of monitored data from additional monitoring systems in determining current fitness activity for a user. In particular, it is advantageous to allow a user to provide additional monitoring systems so that the user incurs the cost of the monitoring systems and receives monitored data indicative of additional body/exercise measurements.

In an example, a user with diabetes may connect a blood sugar monitor to the connection element of exercise machine 38. The blood sugar monitor would advantageously transmit a blood sugar level to exercise machine 38 in the transmittable data format utilized by exercise machine 38. Exercise machine 38 would utilize the blood sugar level, as well as other exercise signals detected by exercise machine 38, in calculating current fitness activity, as will be further described.

At-machine exercise monitor 40 may receive multiple levels of control from any of the independent computing devices. For example, at-machine exercise monitor 40 may only receive personal data from any of the independent computing devices for a particular user. Thereby, at-machine exercise monitor 40 could be initialized for use a particular user, such that at-machine exercise monitor 40 may then adjust any selected exercise programs for the particular user according to the personal data. For example, at an exercise machine that facilitates aerobic activity, if a user's personal data includes age and weight, then a target heart rate for the user will be adjusted for an exercise program selected by the user at at-machine exercise monitor 40. At-machine exercise monitor 40 would determine and transmit a machine control signal according to the exercise program selected by the user and monitor whether or not the user is achieving the target heart rate during exercise.

In another example, at-machine exercise monitor 40 may receive personal data and a selection of a particular exercise program that is stored at at-machine exercise monitory 40. For example, at-machine exercise monitor 40 for a treadmill may include multiple exercise programs that may be selected from, such as a hills exercise program, a fat-burning exercise program and a beginner exercise program. At-machine exercise monitor 40 would determine a machine control signal from the exercise program selection and personal data.

Personal data transmitted from computer system 10 to at-machine exercise monitor 40 is preferably transmitted in an XML data file as shown below, where at-machine exercise monitor 40 is enabled to read the data file. In addition, a predetermined exercise program selection of program "5" for thirty minutes at exercise level "8" may be included in the data file. Moreover, an alternate form of XML formatting may be utilized.

<TimeStamp>888965153</TimeStamp>

<UserID>GeorgeG</UserID>

<Age>30</Age>

<Weight>180</Weight>

<Program>5</Program>

<ProgramTime>003000</ProgramTime>

<ProgramLevel>8</ProgramLevel>

Additionally, at-machine exercise monitor 40 may receive personal data and fitness goals for the user. At-machine exercise monitor 40 is advantageously enabled to determine and specify exercise programs that may be suitable for the user based on the user's personal data and fitness goals. The exercise programs may be specified according to criteria including, but not limited to, an exercise time and exercise intensity.

In particular, a group of diverse types of exercise machines may be produced by a particular manufacturer where the at-machine exercise monitor at any of the group of diverse types of exercise machines specifies exercise programs for that machine and others. For example, a manufacturer may provide a rowing machine, stair climbing machine and upper-body weight lifting machine. A user providing personal data and fitness goals to the at-machine exercise monitor for one of the machines may direct the user to utilize that machine for a particular period of time and then move to another machine for another amount of time in order to achieve the user's fitness goals. In one embodiment of the present invention, as will be described in FIG. 4, each of the exercise machines may include a communication interface, such as a transceiver, such that each of the machines can detect the other machines and such that a specified exercise program at one machine may be transmitted to other machines when the user switches to use the other machines.

In yet another example, at machine-exercise monitor 40 may receive a control program from any of the independent computing devices, wherein at-machine exercise monitor 40 transmits a machine control signal to exercise machine 38 based on the control program. In addition, at-machine exercise monitor 40 would advantageously transmit detected exercise in real-time to any of the independent computing devices being utilized such that the independent computing device determines whether fitness goals and program goals are being met and may adjust the control program in order to aid the user in meeting goals.

Figure 4:
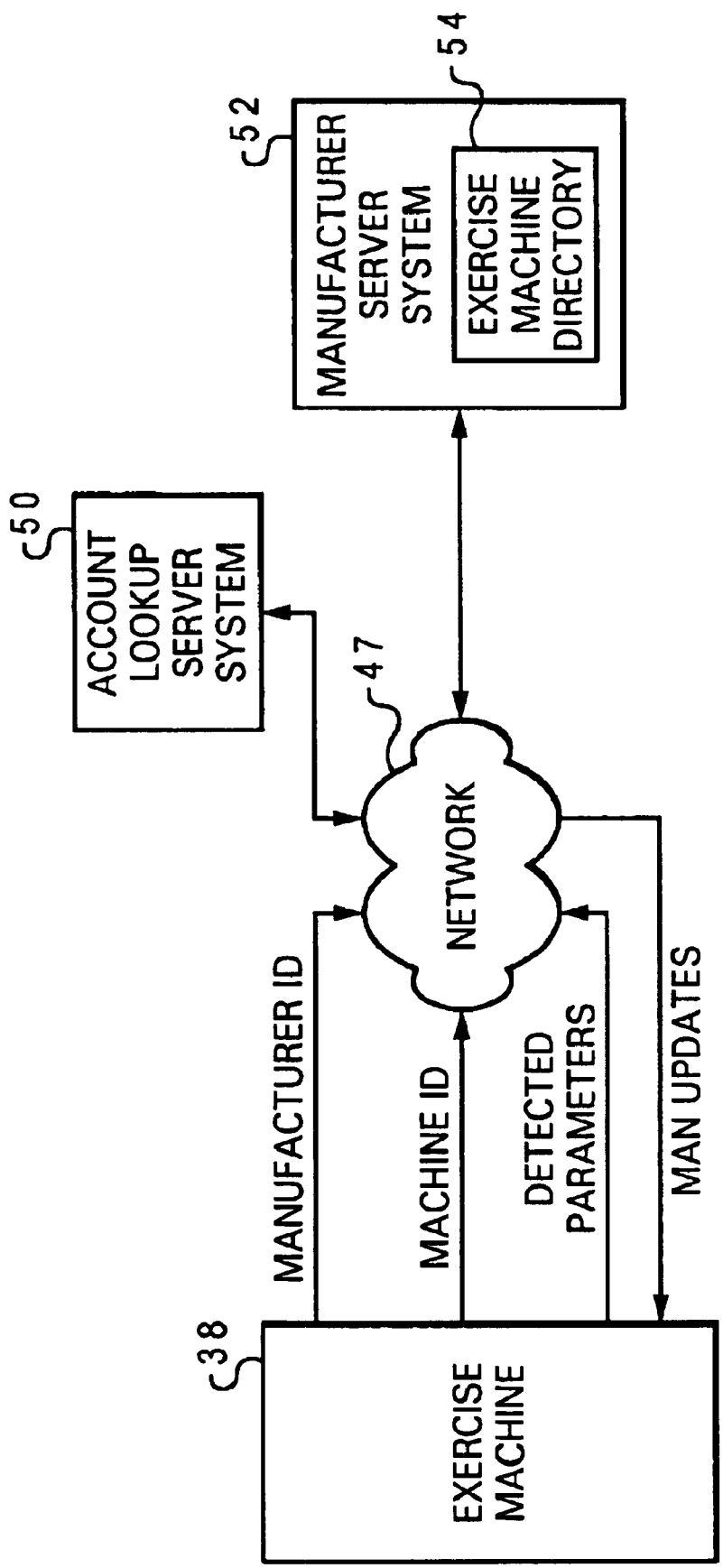
FIG. 4 illustrates a system for monitoring usage of an exercise machine by a manufacturer in accordance with the method, system and program of the present invention.

Referring now to FIG. 4, there is illustrated a system for monitoring usage of an exercise machine by a manufacturer in accordance with the method, system and program of the present invention. As depicted, exercise machine 38 is connected to network 47 via a communication medium, such that a manufacturer identifier, machine identifier and detected parameters are transmitted to network 47 from exercise machine 38. In this case, the communication medium might utilize a transceiver provided by the manufacturer at an exercise machine, such that the manufacturer incurs any costs related to communicating via network 47. In addition, the transceiver may be equipped with a global positioning system that detects the position of exercise machine 38, such that the location of exercise machine 38 is transmittable. Alternatively, when a customer first initiates use of exercise machine 38, the user may be prompted to enter a location for exercise machine 38 or register a location with the manufacturer.

The manufacturer identifier is advantageously looked up in an account lookup server system 50 to identify the address of the server system associated with the manufacturer identifier. The machine identifier and detected parameters are then routed to the address of the identified server system, in this case manufacturer server system 52. In particular, a manufacturer identifier may be associated with a groups including, but not limited to, a particular manufacturer of an exercise machine, authorized dealers of an exercise machine or a health club that owns the machine.

Manufacturer server system 52 advantageously includes an exercise machine directory 54 that includes a database of the machine identifiers for multiple exercise machines enabled for monitoring at manufacturer server system 52. Preferably data received at manufacturer server system 52 is stored according to the machine identifier associated with the data. In addition, the directory may include a registered location of an exercise machine and advantageously tracks the usage of a particular exercise machine by location. For example, if within a health club a machine is moved around to multiple positions, the usage of the machine at each of the locations is preferably stored and retrievable in order to compare location dependent usage rates.

Detected parameters preferably include data such as the length of usage by one user, the amount of uses each hour, which exercise programs are selected, user identifiers, the location of the machine and other data which might be useful for a manufacturer of an exercise machine. Therefore, manufacturer server system 52 is advantageously enabled to store information about how exercise machine 38 is being utilized in order to better manufacture future exercise machines and possibly provide upgrades to current machines. For example, if a particular software bug is detected for a particular type of machine, an exercise machine manufacturer may transmit an updated version of software by a manufacturer update(MAN UPDATE). In another example, if a manufacturer develops a new game application for display from an at-machine exercise monitor, the game application may be transmitted by a manufacturer update. Additionally, a user may register with a manufacturer and pay to receive a machine update, such as an additional game application for display.

Figure 5:
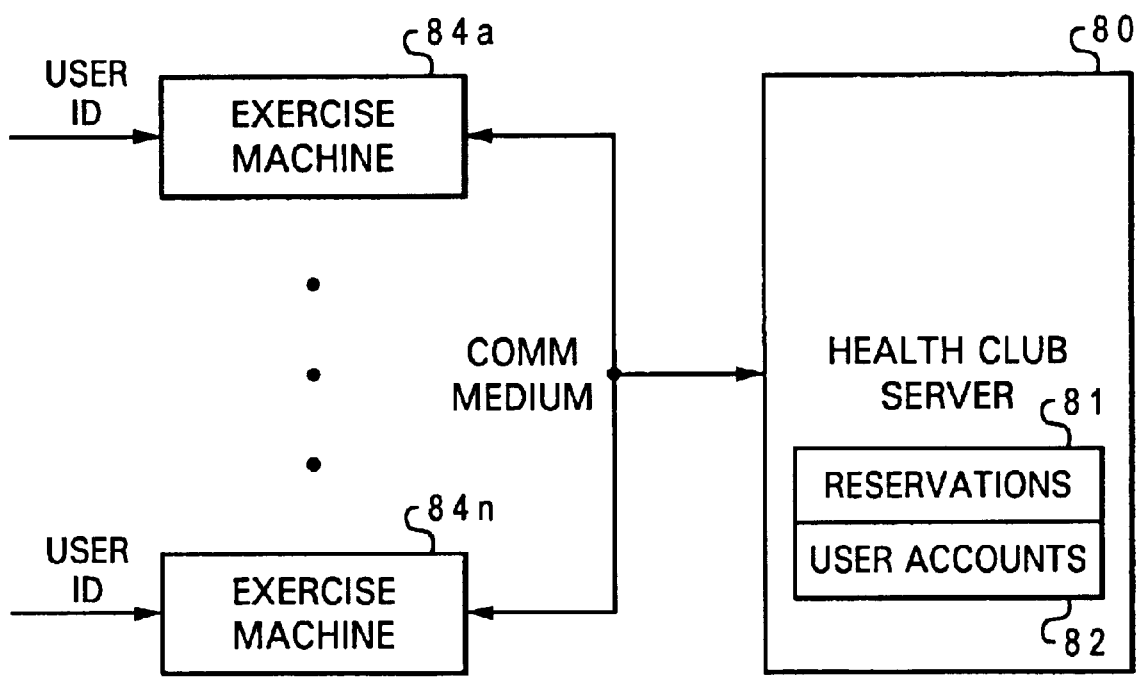
FIG. 5 depicts one embodiment of a block diagram of a machine usage system for a health club in accordance with the method, system and program of the present invention.

Referring now to FIG. 5, there is illustrated a block diagram of a machine usage system for a health club in accordance with the method, system and program of the present invention. Health club server 80 preferably includes a reservation database 81 containing a listing of each exercise machine available and any reservations made for the machines. In addition, time limits for each exercise machine may be specified. In addition, health club server 80 preferably includes user accounts 82 that may include a prepaid debit amount, a credit card number, bank account number, or other financial information that can be utilized to charge a user for a particular service.

Health club server 80 may be connected to multiple exercise machines 84a–84n via a communications medium. Exercise machines 84a–84n receive a reservation identifier or user identifier for the user and transmit verification requests to health club server 80 to verify that a user has a reservation for an exercise monitor being requested by that user. In verifying a user, both the reservation stored in reservation database 81 and the account information for the user stored in user accounts 82 are verified. In addition, the user account may be debited. In receiving a verification, exercise machines 84a–84n are enabled to function for the verified user.

Figure 6:
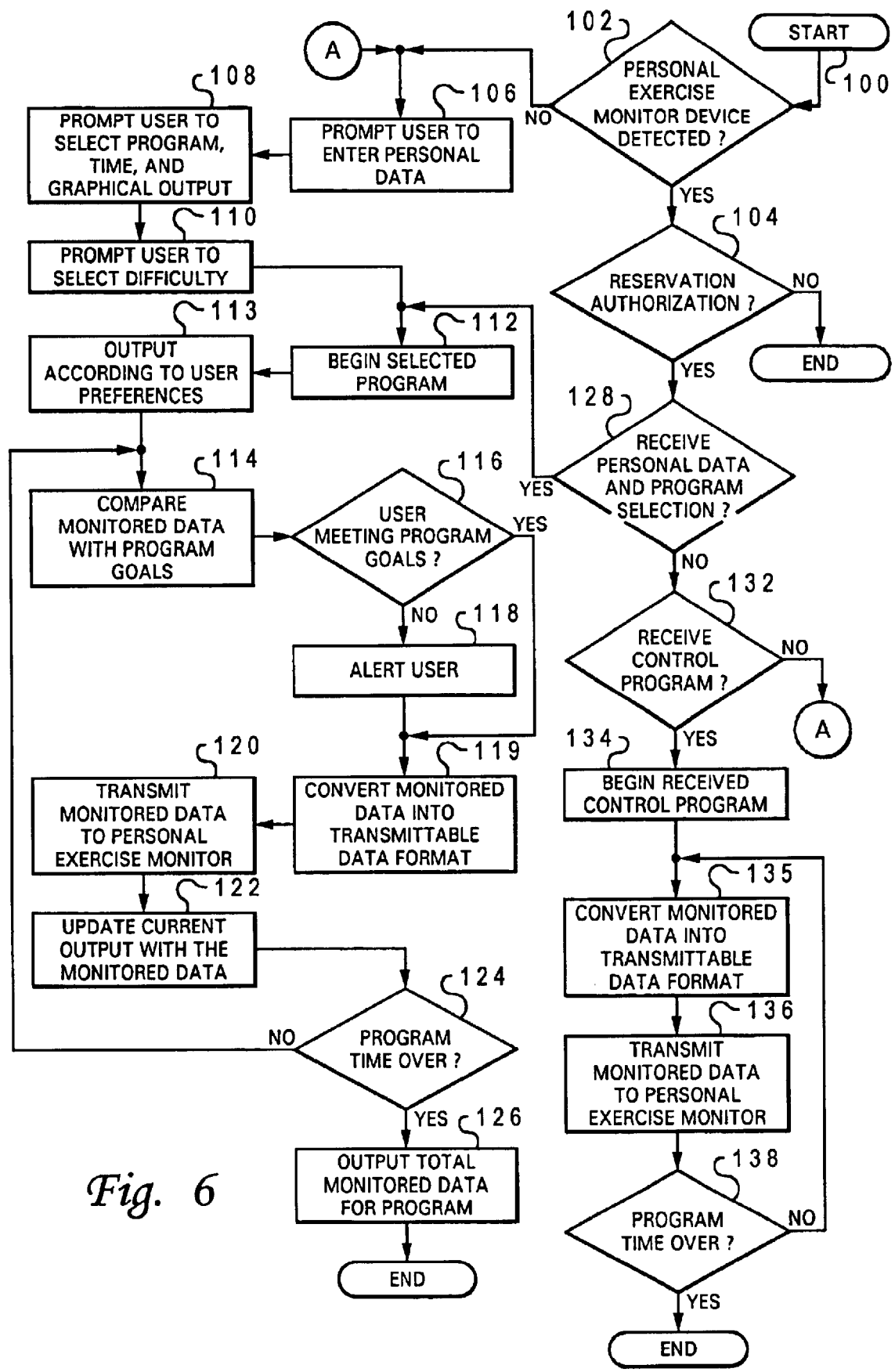
FIG. 6 illustrates a high level logic flowchart of a process and program for controlling an exercise machine in accordance with the present invention.

With reference now to FIG. 6, there is illustrated a high level logic flowchart of a process and program for controlling an exercise machine in accordance with the present invention. As depicted, the process starts at block 100 and thereafter proceeds to block 102. Block 102 illustrates a determination as to whether or not reservation authorization is received. In order for reservation authorization to be received the user must enter an identifier into a machine monitor or supply the identifier from a personal exercise monitor. If a reservation for the machine has been made, the identifier is compared with an identifier under which the machine is reserved. If there is a match, authorization is provided. Therefore, if authorization is not provided, the process ends. If authorization is provided, the process passes to block 104. Block 104 depicts a determination as to whether or not a personal exercise monitor is selected to control the exercise machine. If a personal exercise monitor is not selected, the process passes to block 106. If a personal exercise monitor is selected, the process passes to block 128.

Block 106 illustrates prompting the user to enter personal data such as age, weight, and height. Thereafter, block 108 depicts prompting the user to select a program, time duration and output preference for the program. Next, block 110 illustrates prompting the user to select a difficulty or speed of the program. Thereafter, block 112 depicts starting the selected program. Block 113 depicts controlling output of the monitored data and any other user-determined output according the user's output preferences to an output interface. Block 114 illustrates comparing monitored data with program goals. Next, block 116 depicts a determination as to whether or not the user is meeting the program goals. For example, meeting a program goal might include that a user's heart rate has reached a target level depending on the age and weight of the user. If the user is meeting the program goals, then the process passes to block 119. If the user is not meeting the program goals, then the process passes to block 118. Block 118 illustrates alerting the user that they are not within the program goals. The user is not within the program goals if the user does not reach the program goals or if the user exceeds the program goals. Next, block 119 depicts converting the monitored data into a common transmittable data format. Block 120 illustrates transmitting the monitored data to the personal exercise monitor. Thereafter, block 122 illustrates updating the current output with the monitored data. Next, block 124 depicts a determination as to whether or not the program for the machine is over. If the program is not over, the process passes to block 114. If the program is over, the process passes to block 126. Block 126 illustrates outputting totals of monitored data from the duration of the exercise program; and the process ends.

Returning to block 128, there is depicted a determination as to whether or not personal data and program selection are received. If personal data and program selection are received, then the process passes to block 112 and are utilized to set-up the at-machine exercise monitor. If personal data and program selection are not received, the process passes to block 132. Block 132 illustrates a determination as to whether or not a control program signal from a personal exercise monitor is received. If a control program signal is not received, the process defaults and passes to block 106. If a control program signal is received, the process passes to block 134. Block 134 depicts starting control of the exercise machine by the control program signal. Thereafter, block 135 illustrates converting the monitored exercise data into a common transmittable data format. Next, block 136 depicts transmitting monitored exercise data to the personal exercise monitor. Next, block 138 illustrates a determination as to whether the program time is over as designated by the control signal. If the program time is over, the process ends. If the program time is not over, the process passes to block 136.

It is important to note that, although the present invention has been described in the context of a fully functional computer controlled exercise machine, those skilled in the art will appreciate that the mechanisms of the present invention are capable of being distributed as a program product in a variety of forms, and that the present invention applies equally regardless of the particular type of signal-bearing media utilized to actually carry out the distribution. Examples of signal-bearing media include, but are not limited to, recordable-type media such as floppy disks or CD-ROMs and transmission-type media such as analogue or digital communications links.

While the invention has been particularly shown and described with reference to a preferred embodiment, it will be understood by those skilled in the art that various changes in form and detail may be made therein without departing from the spirit and scope of the invention.

What is claimed is:

1. A method for controlling an exercise machine, said method comprising the steps of:
   receiving exercise-related data for a particular user at an exercise machine via a communication interface s with an independent computing device specified by said particular user; and
   specifying control of said exercise machine according to said exercise-related data for said particular user, such that a particular level of control of said exercise machine is specified according to exercise-related data for said particular user from said independent computing device.

2. The method for controlling an exercise machine according to claim 1, wherein said step of receiving exercise-related data for a particular user at an exercise machine via a communication interface with an independent computing device specified by said particular user, further comprises the step of:
   receiving said exercise-related data for said particular user via said communication interface with a portable computer system provided by said particular user.

3. The method for controlling an exercise machine according to claim 1, wherein said step of receiving exercise-related data for a particular user at an exercise machine via a communication interface with an independent computing device specified by said particular user, further comprises the step of:
   receiving said exercise-related data for said particular user via said communication interface with a personal storage device proffered by said particular user.

4. The method for controlling an exercise machine according to claim 1, wherein said step of receiving exercise-related data for a particular user at an exercise machine via a communication interface with an independent computing device specified by said particular user, further comprises the step of:
   receiving said exercise-related data for said particular user via a network from a universally accessible server system according to a particular universal identifier associated with said particular user.

5. The method for controlling an exercise machine according to claim 1, wherein said step of receiving exercise-related data for a particular user at an exercise machine via a communication interface with an independent computing device specified by said particular user, further comprises the step of:
   receiving personal data for said particular user at said exercise machine from said independent computing device.

6. The method for controlling an exercise machine according to claim 1 wherein said step of receiving exercise-related data for a particular user at an exercise machine via a communication interface with an independent computing device specified by said particular user, further comprises the step of:
   receiving fitness goals for said particular user at said exercise machine from said independent computing device.

7. The method for controlling an exercise machine according to claim 1, wherein said step of receiving exercise-related data for a particular user at an exercise machine via a communication interface with an independent computing device specified by said particular user, further comprises the step of:
   receiving a control program for said particular user at said exercise machine from said independent computing device.

8. The method for controlling an exercise machine according to claim 1, wherein said step of specifying control of said exercise machine according to said exercise-related data for said particular user, further comprises the step of:
   specifying control of said exercise machine according to a control program signal received at said exercise machine for said particular user.

9. The method for controlling an exercise machine according to claim 1, wherein said step of specifying control of said exercise machine according to said exercise-related data for said particular user, further comprises the step of:
   specifying control of said exercise machine by an at-machine exercise machine monitor that is an interface to said exercise machine.

10. The method for controlling an exercise machine according to claim 9, said method further comprises the step of:
    specifying a time duration and intensity for exercise at said at-machine exercise machine monitor according to fitness goals comprised in said exercise-related data.

11. The method for controlling an exercise machine according to claim 1, said method further comprising the step of:
    computing current fitness activity for said particular user according to said exercise-related data for said particular user.

12. The method for controlling an exercise machine according to claim 1, said method further comprising the step of:
    controlling output of indicators of fitness activity by said particular user from said exercise machine to an output interface according to user output preferences included in said exercise-related data.

13. The method for controlling an exercise machine according to claim 1, said method further comprising the step of:

enabling a removable output interface coupled to said exercise machine to output indicators of fitness activity by said particular user from said exercise machine.

14. The method for controlling an exercise machine according to claim 1, said method further comprising the step of:

enabling a removable monitoring system coupled to said exercise machine to detect indicators of fitness activity by said particular user and transmit said indicators of fitness activity to said exercise machine.

* * * * *

(12) EX PARTE REEXAMINATION CERTIFICATE (10709th)
United States Patent
Brown et al.

(10) Number: US 6,702,719 C1
(45) Certificate Issued: Sep. 11, 2015

(54) EXERCISE MACHINE

(75) Inventors: Michael Wayne Brown, Georgetown, TX (US); Kelvin Roderick Lawrence, Round Rock, TX (US); Michael A. Paolini, Round Rock, TX (US)

(73) Assignee: ICON HEALTH & FITNESS, INC., Logan, UT (US)

Reexamination Request:
No. 90/013,350, Sep. 23, 2014

Reexamination Certificate for:
Patent No.: 6,702,719
Issued: Mar. 9, 2004
Appl. No.: 09/561,422
Filed: Apr. 28, 2000

(51) Int. Cl.
*A63B 22/00* (2006.01)
*G06F 19/00* (2011.01)
*A63B 24/00* (2006.01)

(52) U.S. Cl.
CPC ............ *A63B 22/00* (2013.01); *G06F 19/3481* (2013.01); *A63B 2220/833* (2013.01); *A63B 2225/20* (2013.01); *A63B 2225/30* (2013.01); *A63B 2230/06* (2013.01)

(58) Field of Classification Search
None
See application file for complete search history.

(56) References Cited

To view the complete listing of prior art documents cited during the proceeding for Reexamination Control Number 90/013,350, please refer to the USPTO's public Patent Application Information Retrieval (PAIR) system under the Display References tab.

*Primary Examiner* — Peter C English

(57) ABSTRACT

In accordance with the present invention, an exercise machine receives exercise-related data for a particular user via a communication interface with an independent computing device specified by the particular user, such as a portable computer system, personal storage device, or network system. The exercise machine specifies control of the exercise machine according to the exercise-related data for the particular user, such that a particular level of control of the exercise machine is specified according to exercise-related data for the particular user from the independent computing device. In addition, the exercise machine transmits indicators of usage of the exercise machine to a server system that may be utilized by a manufacturer to track the usage of a particular exercise machine.

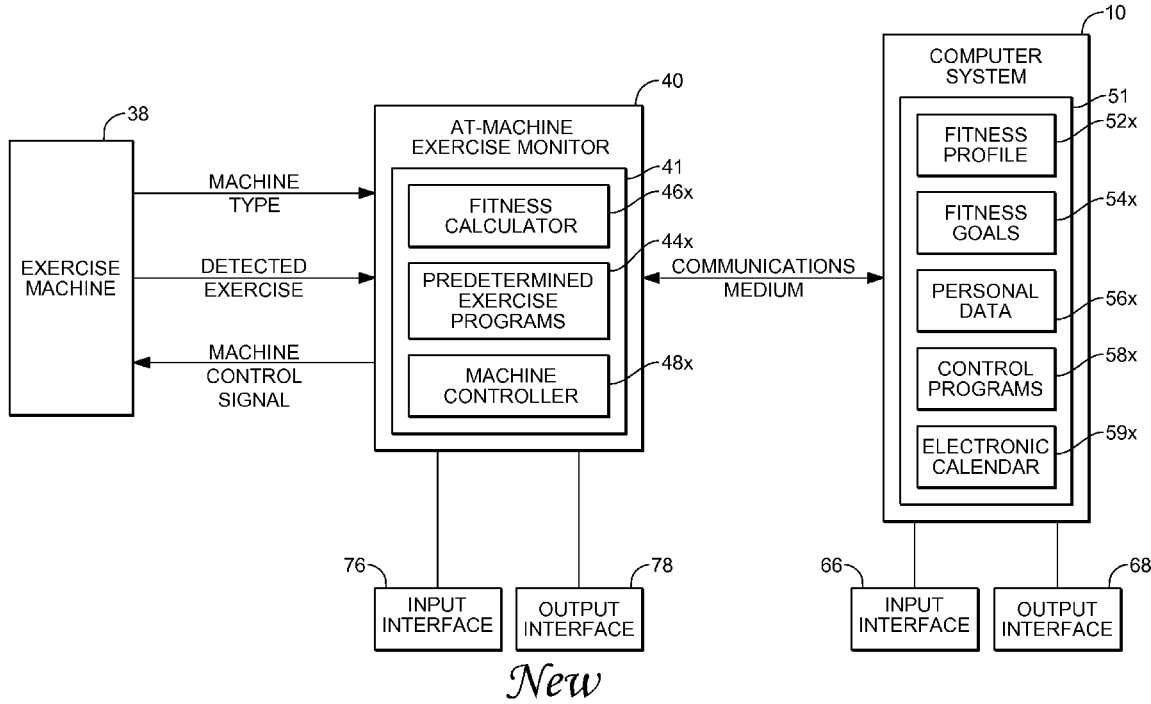

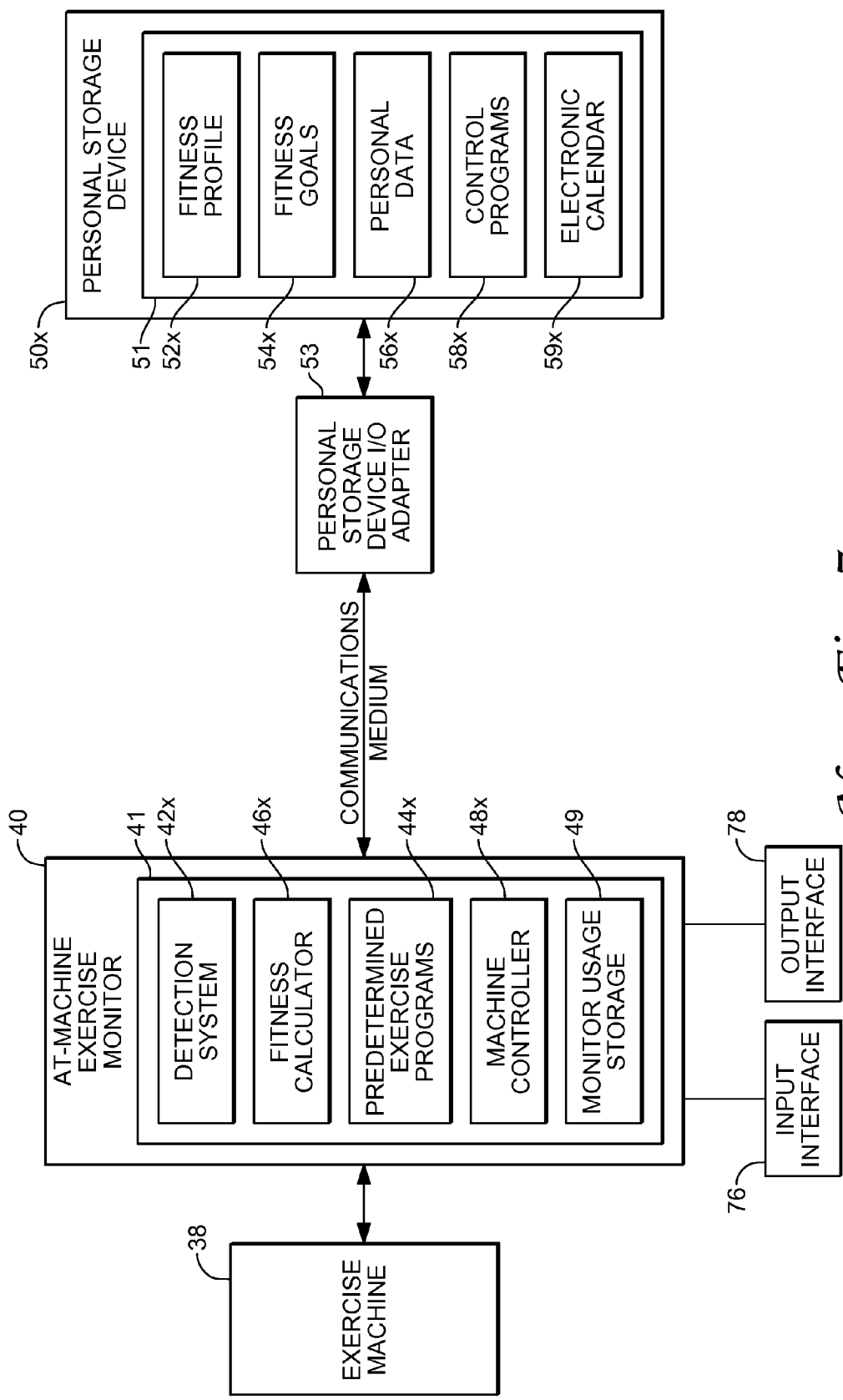
New Fig. 7

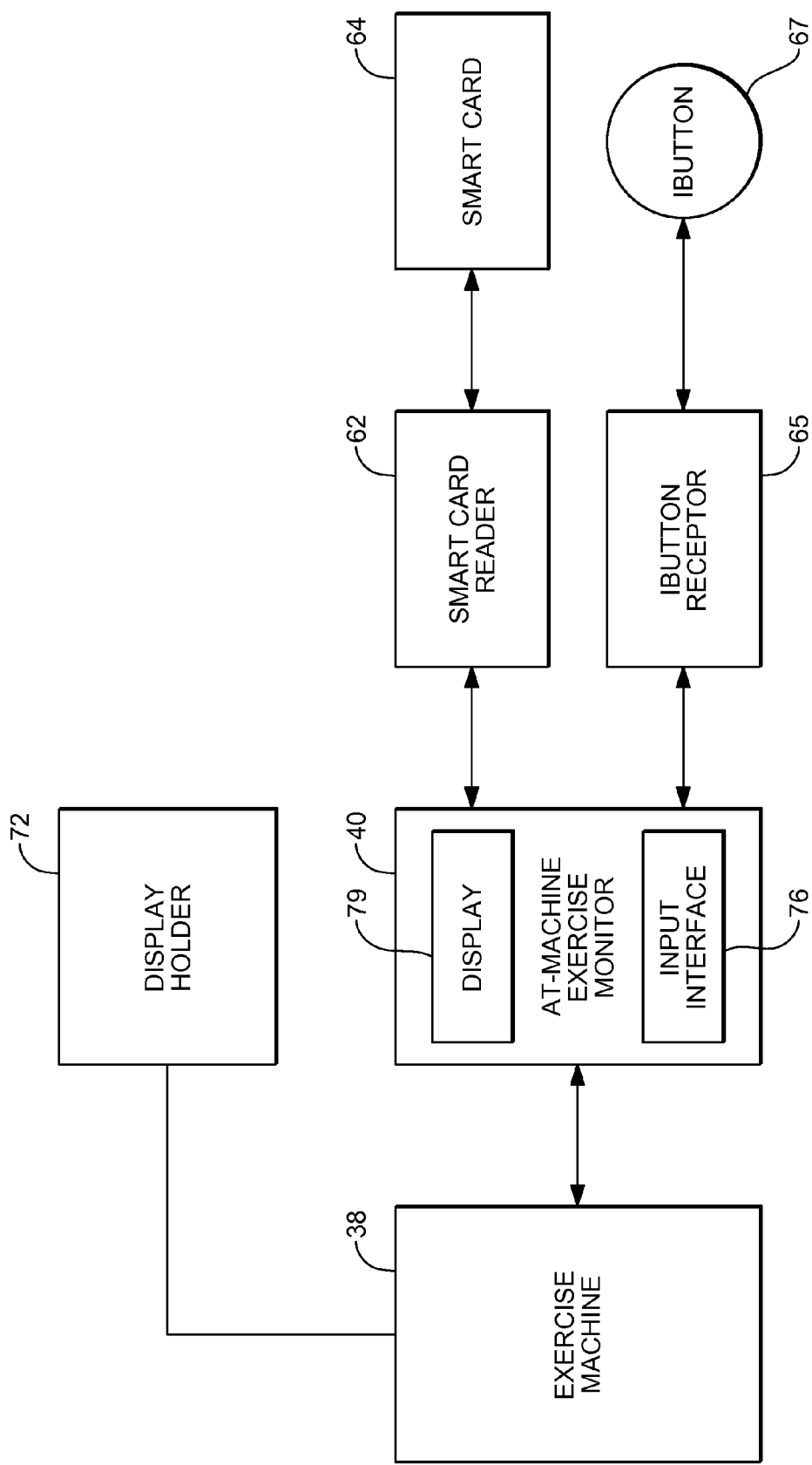

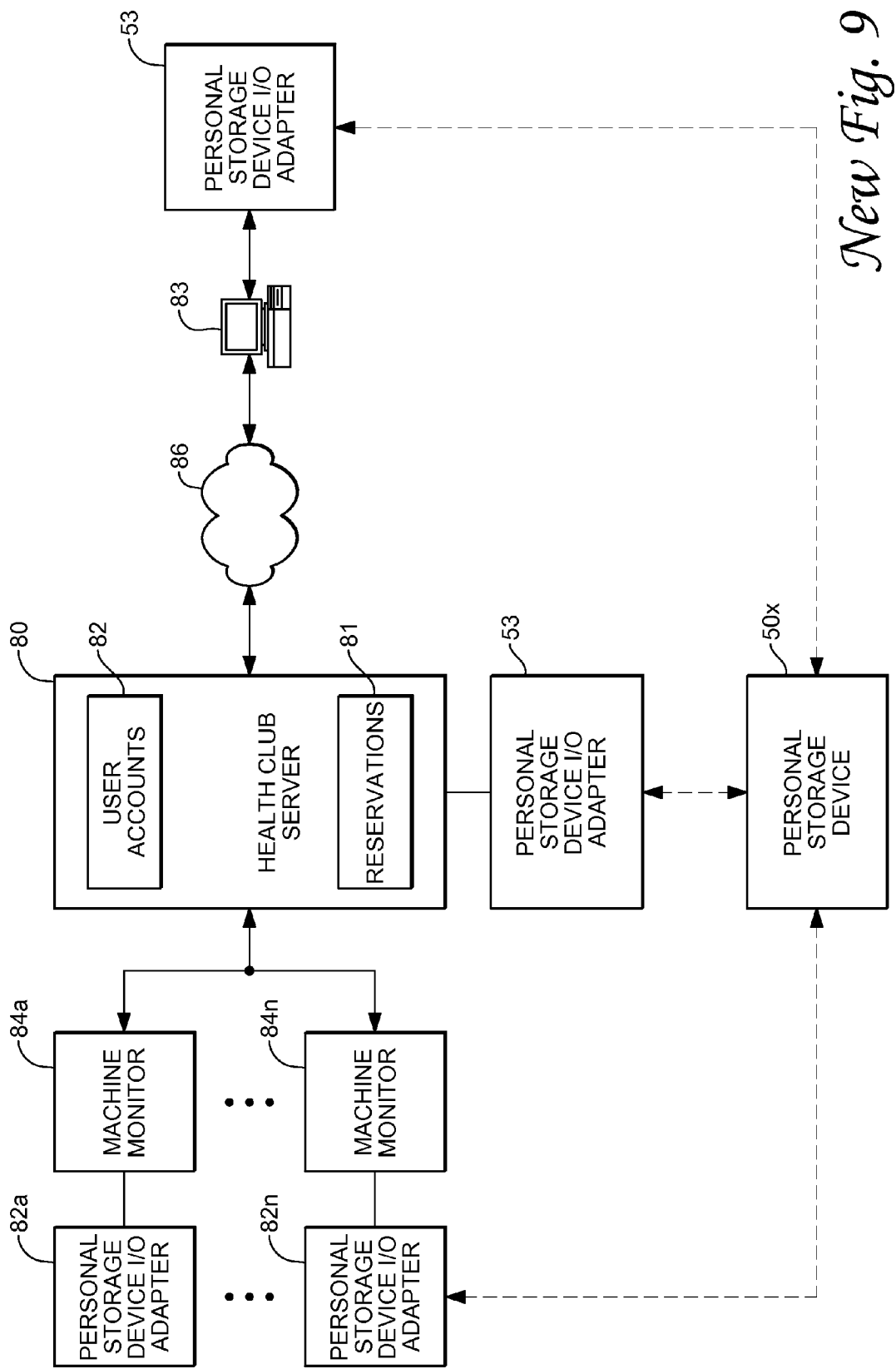

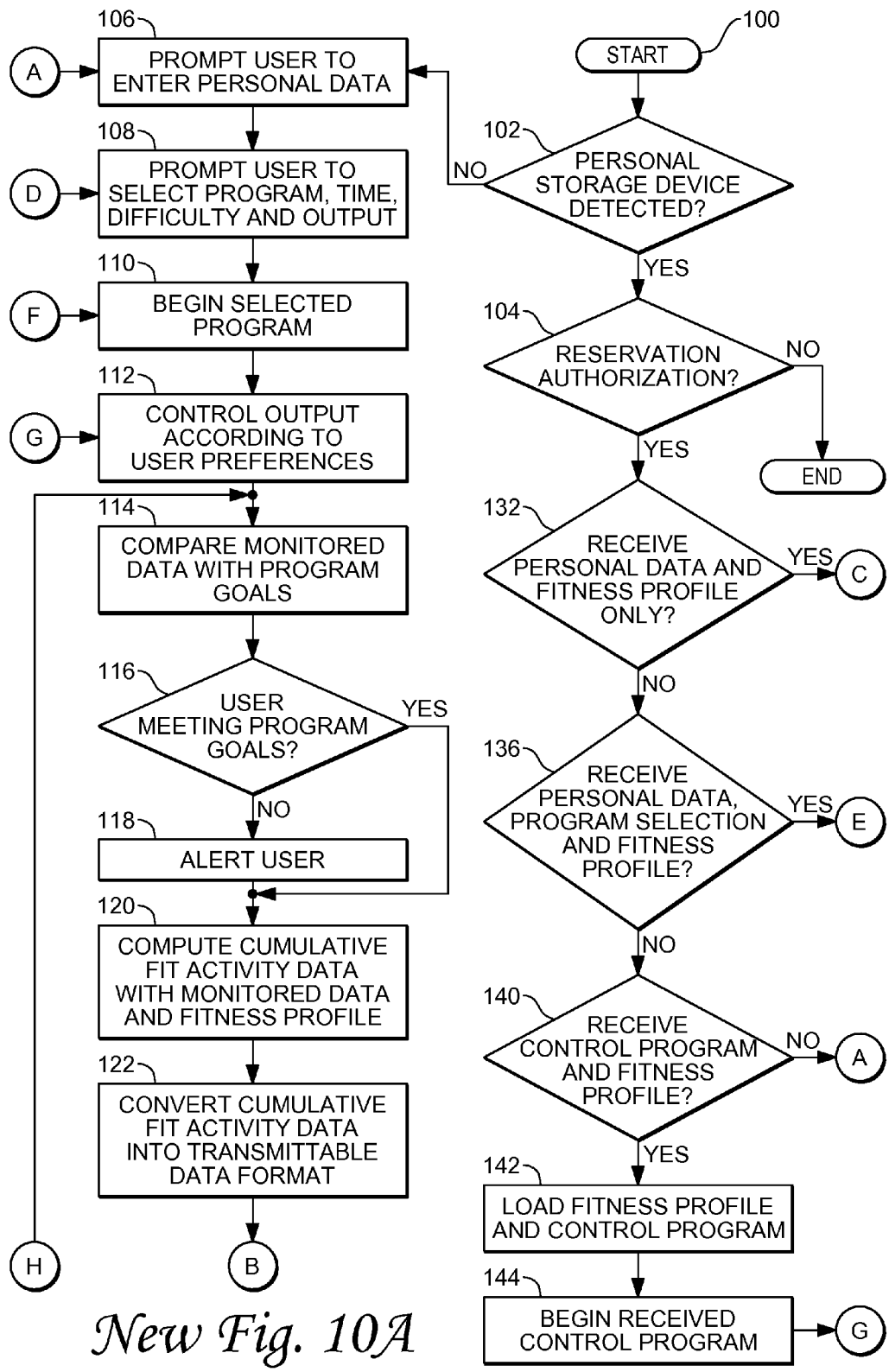
New Fig. 10A

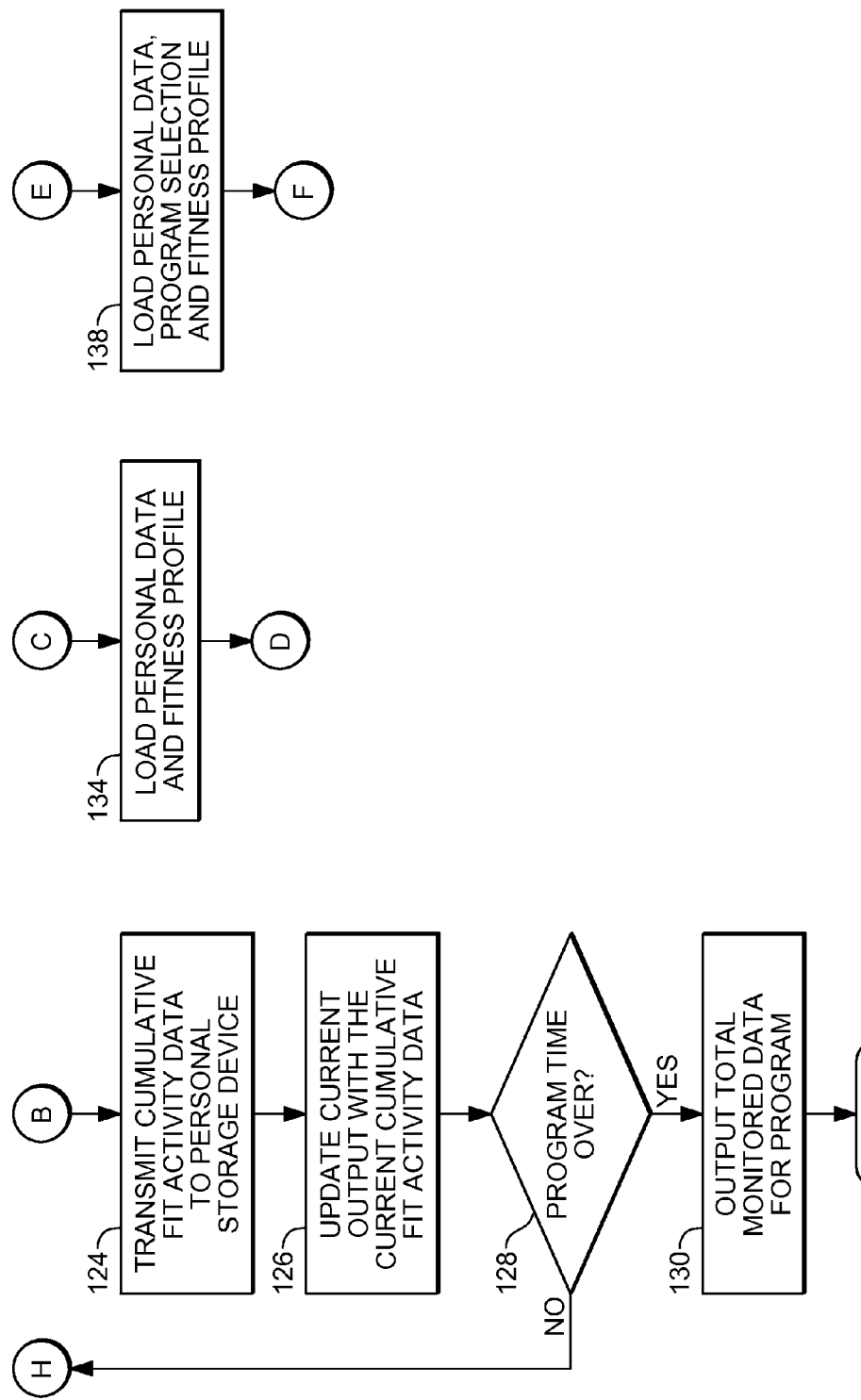
New Fig. 10B

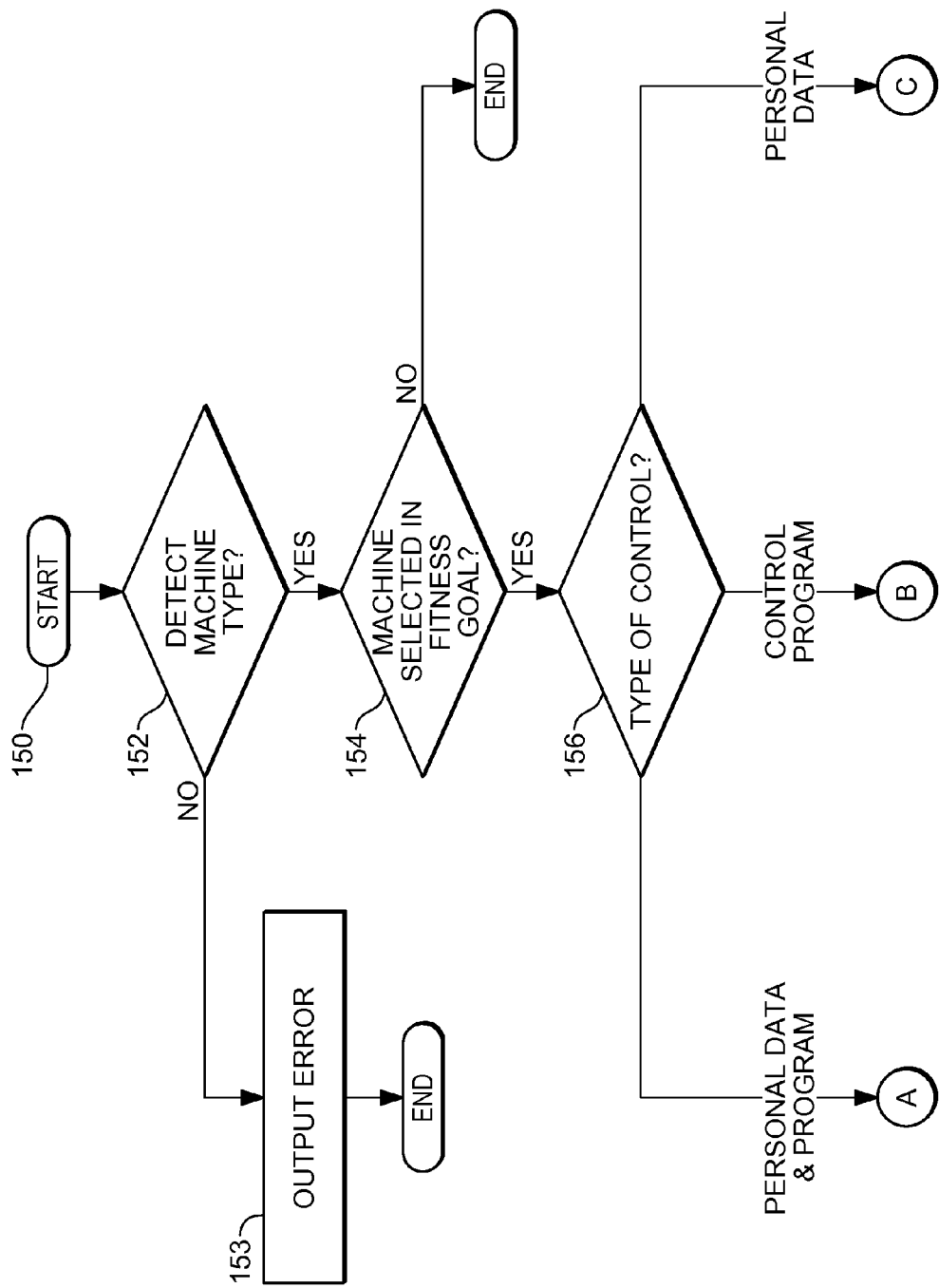
New Fig. 11A

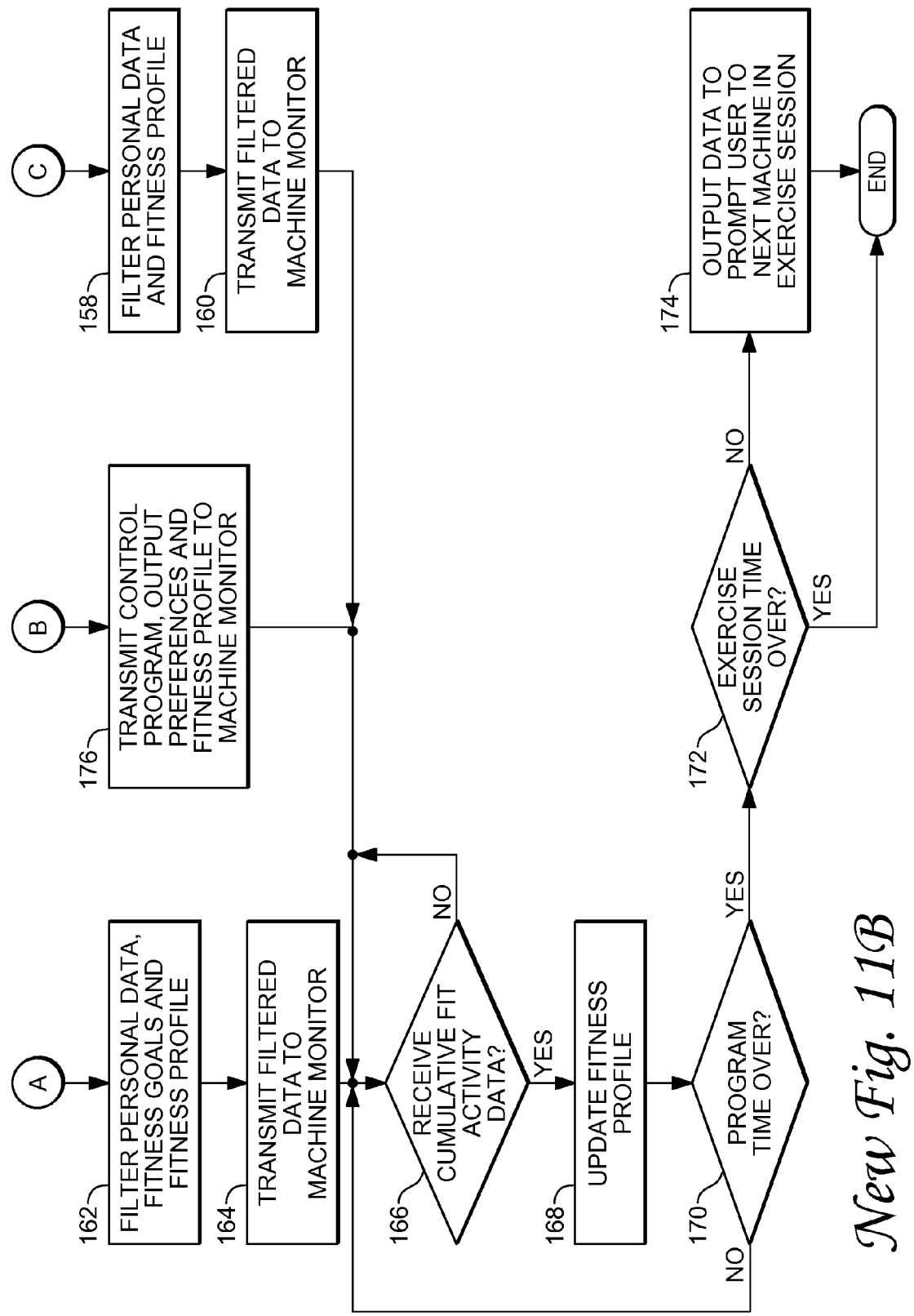
New Fig. 11B

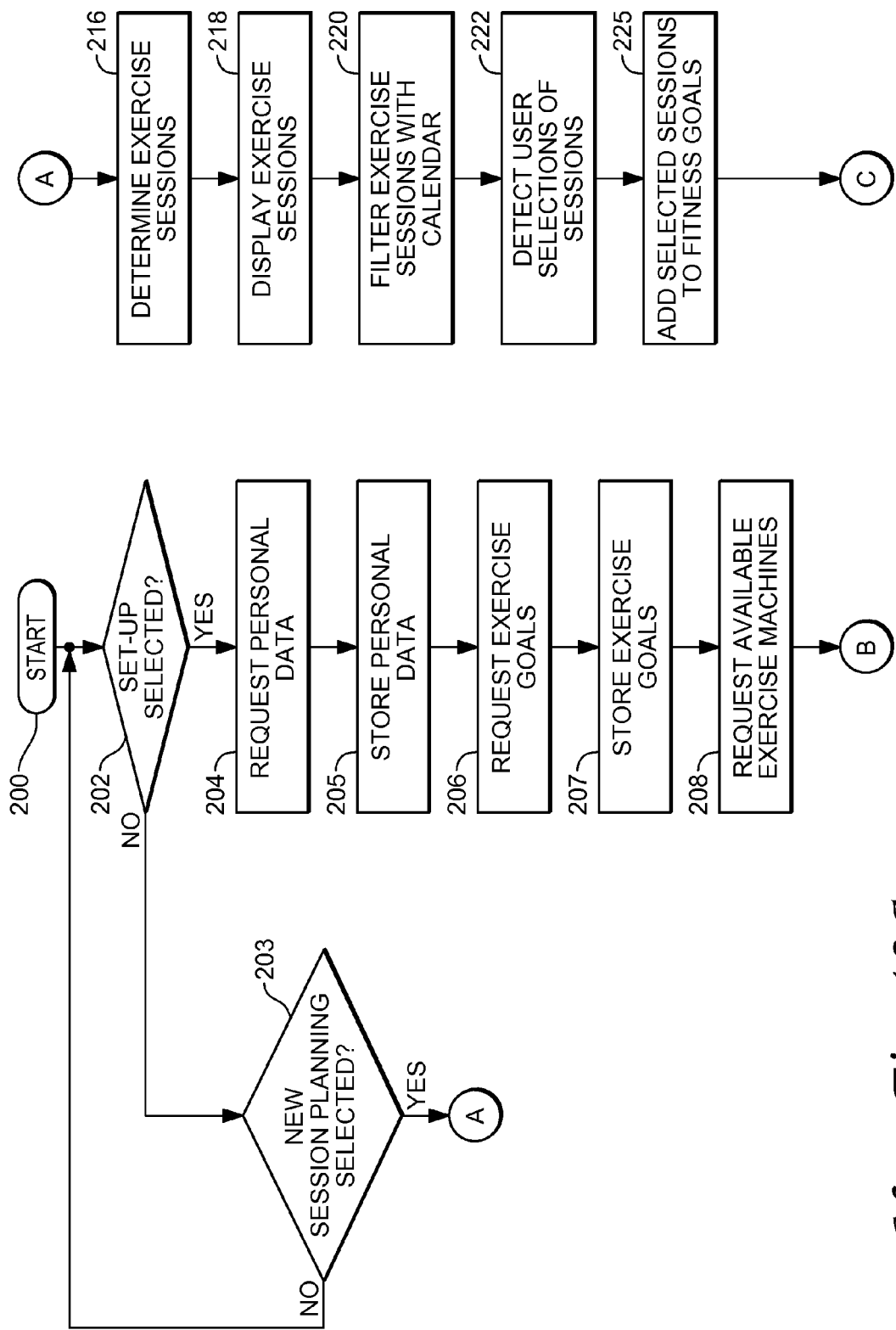
New Fig. 12A

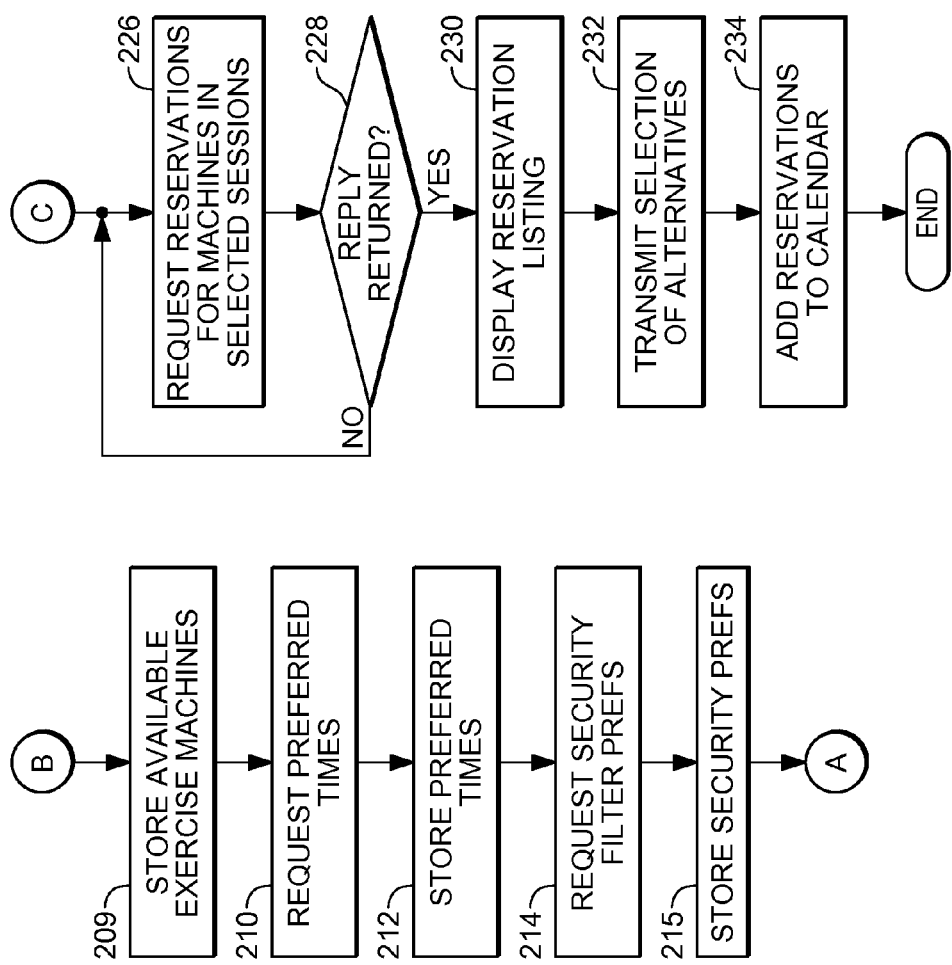
New Fig. 12B

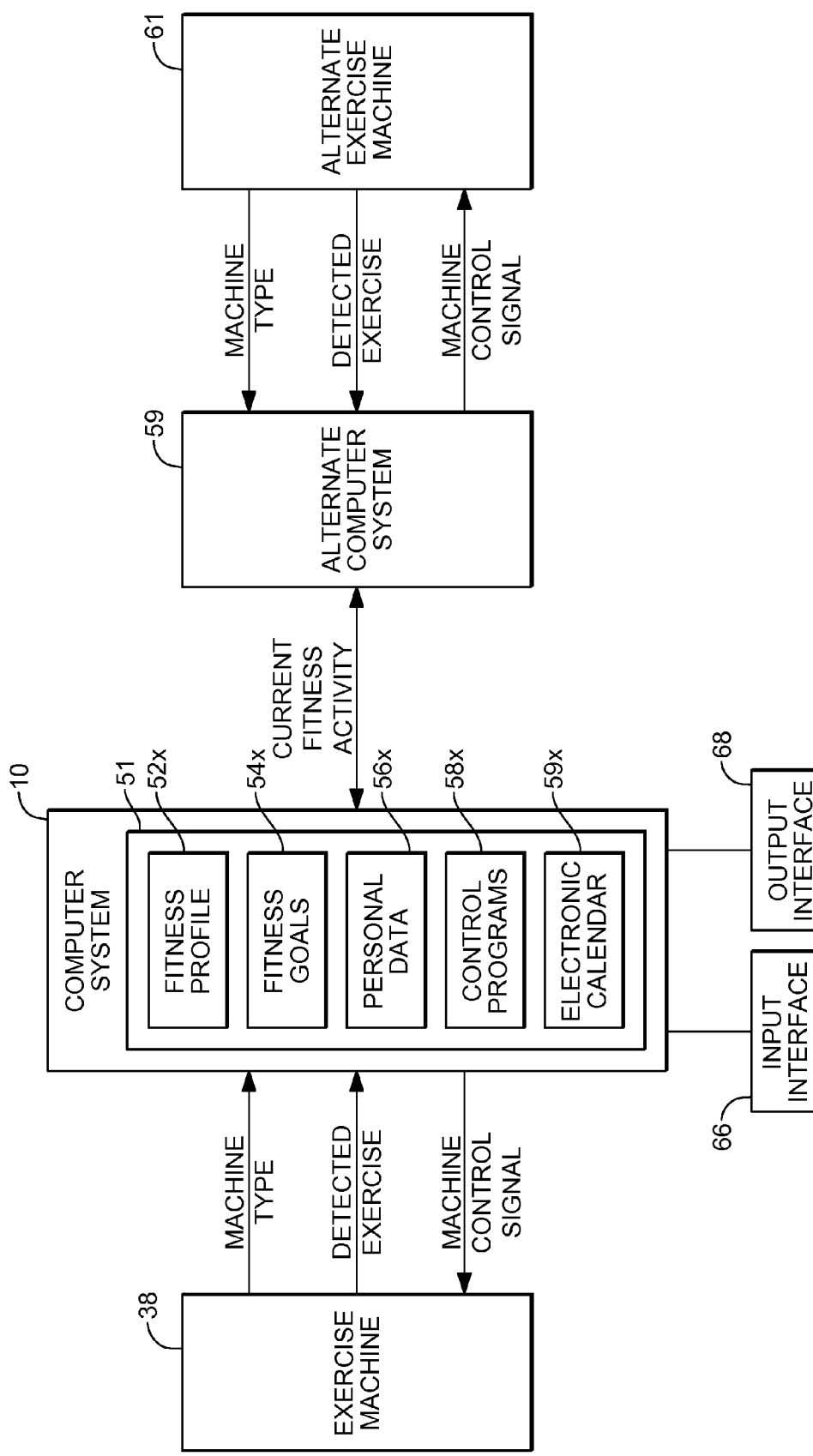

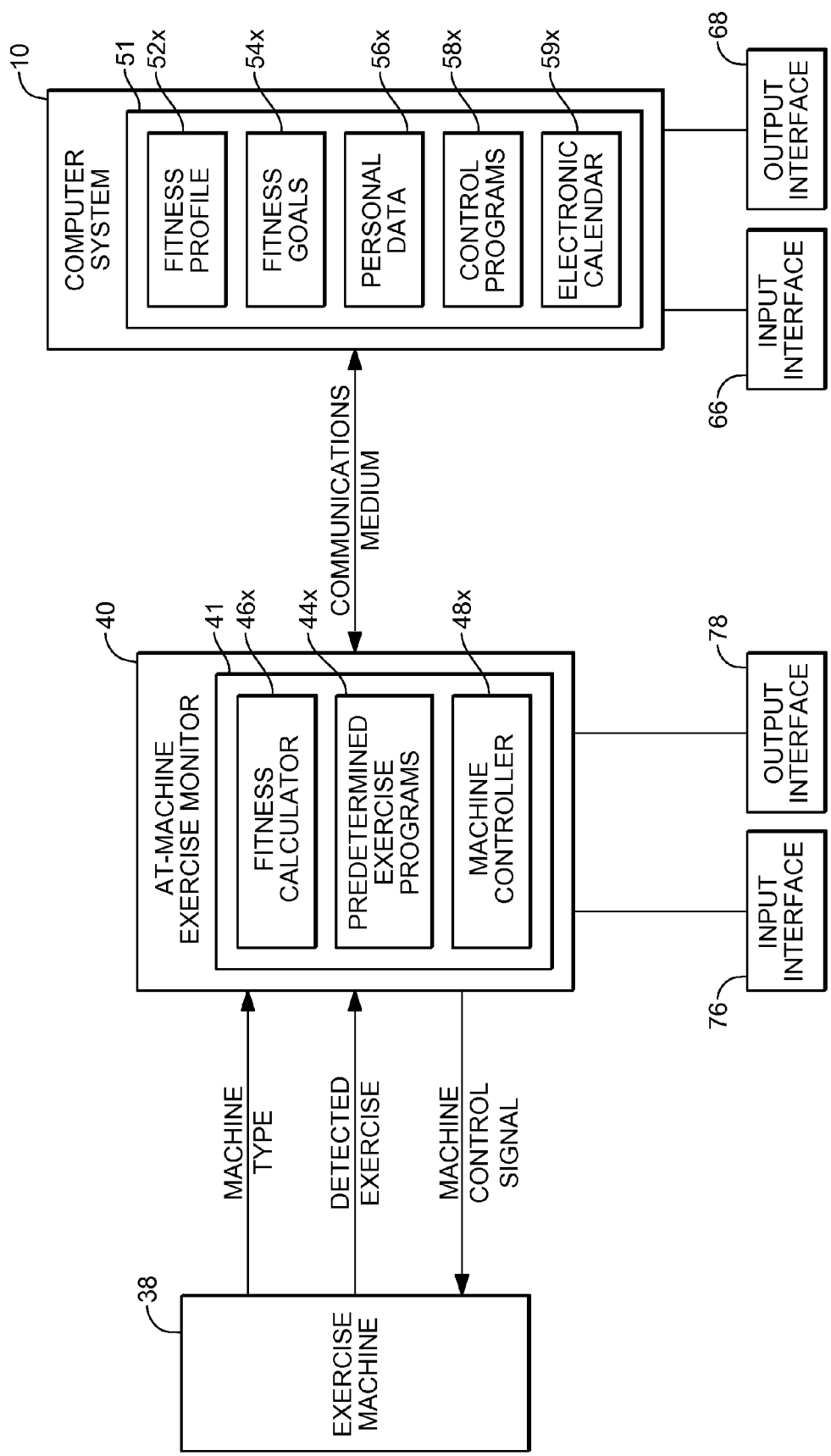
New Fig. 14

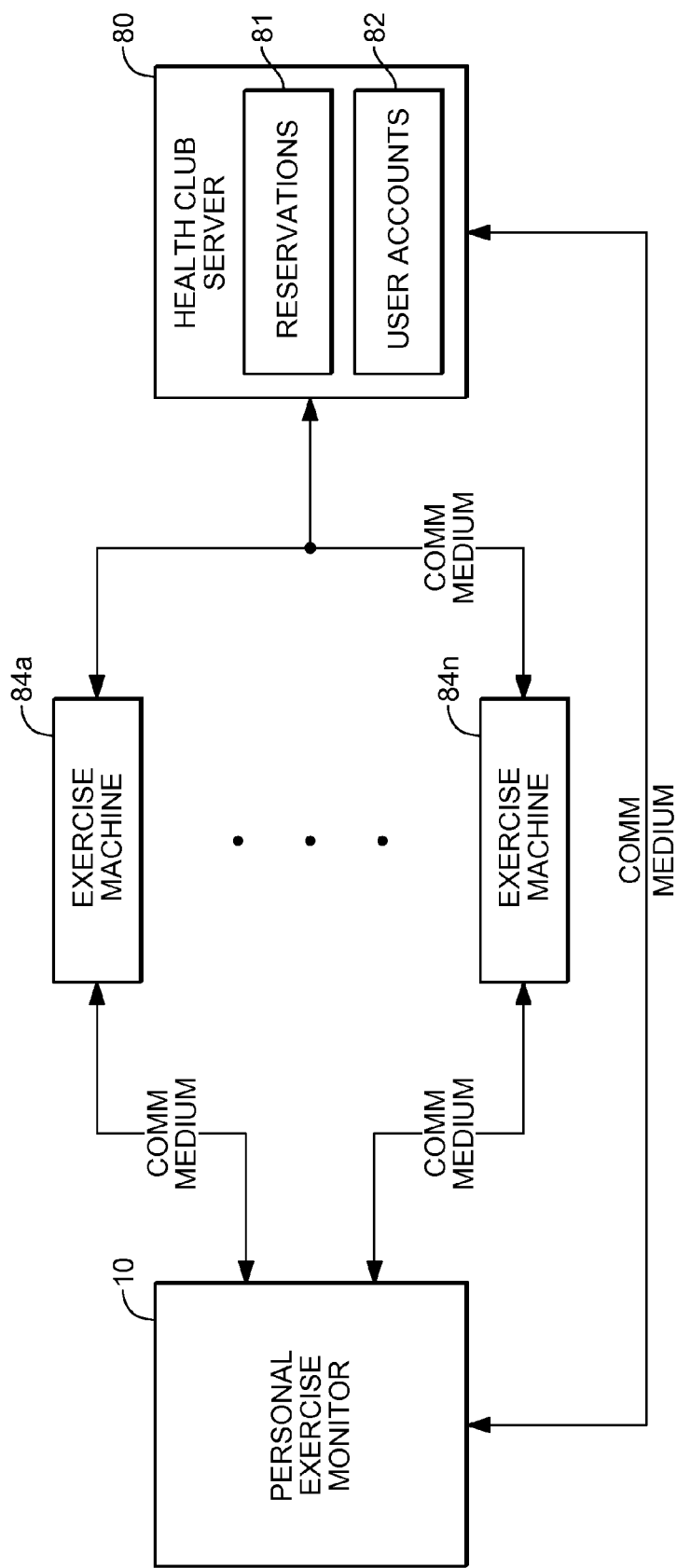
New Fig. 15

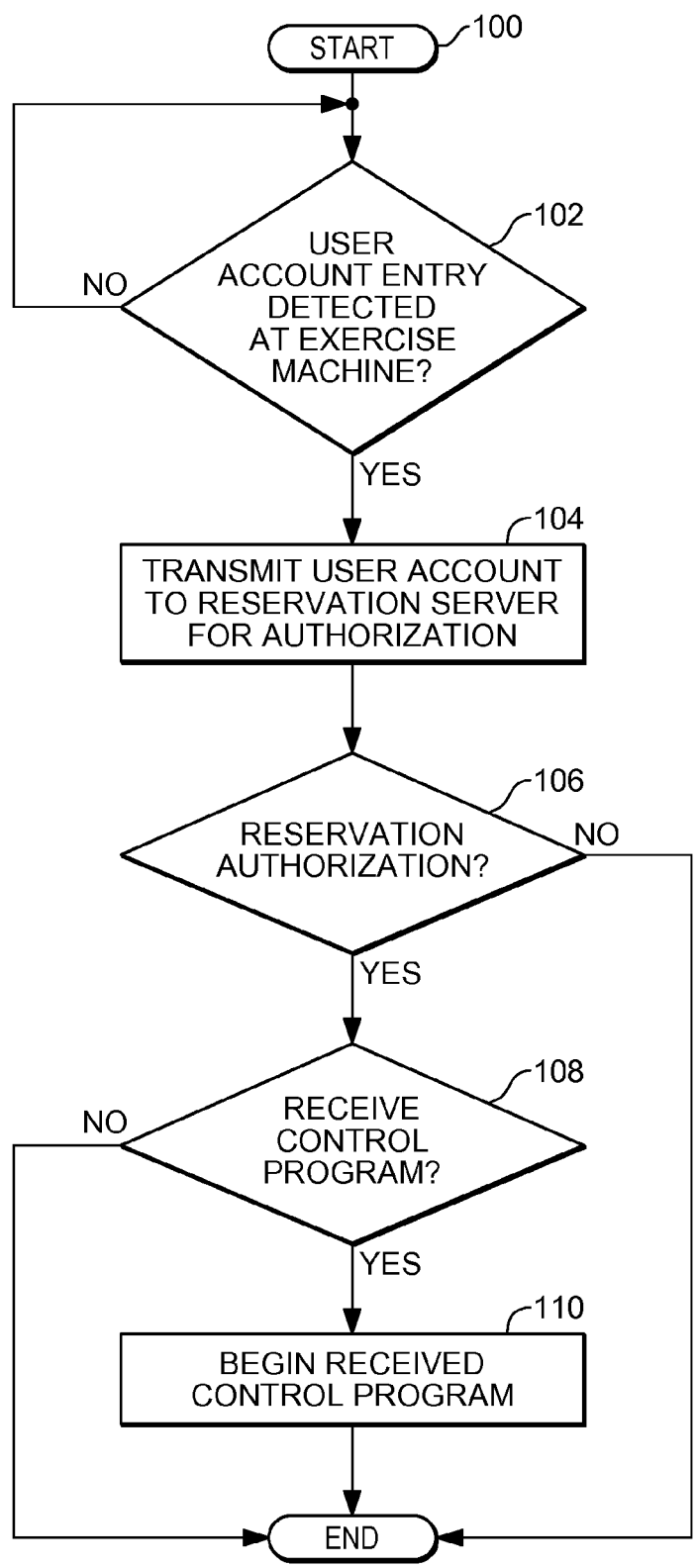
*New Fig. 16*

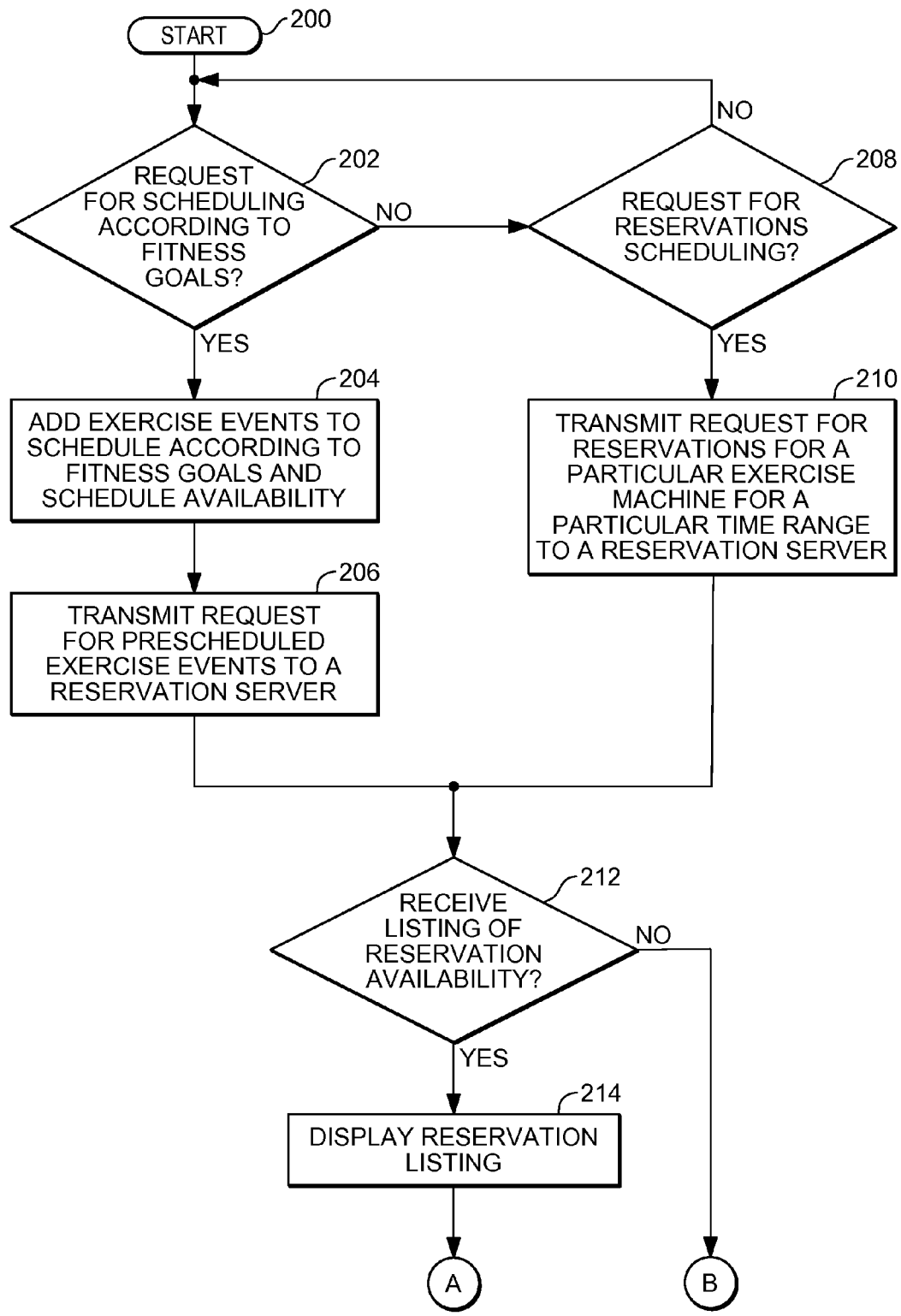
*New Fig. 17A*

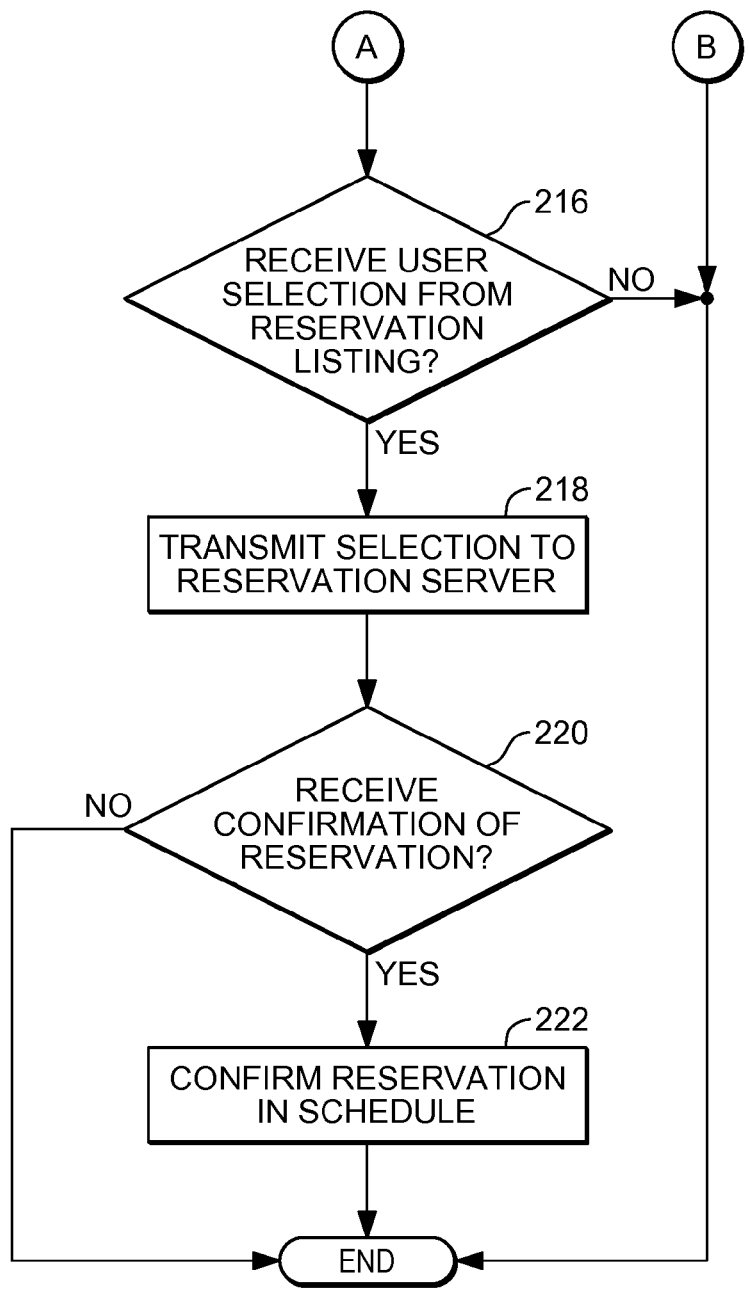
New Fig. 17B

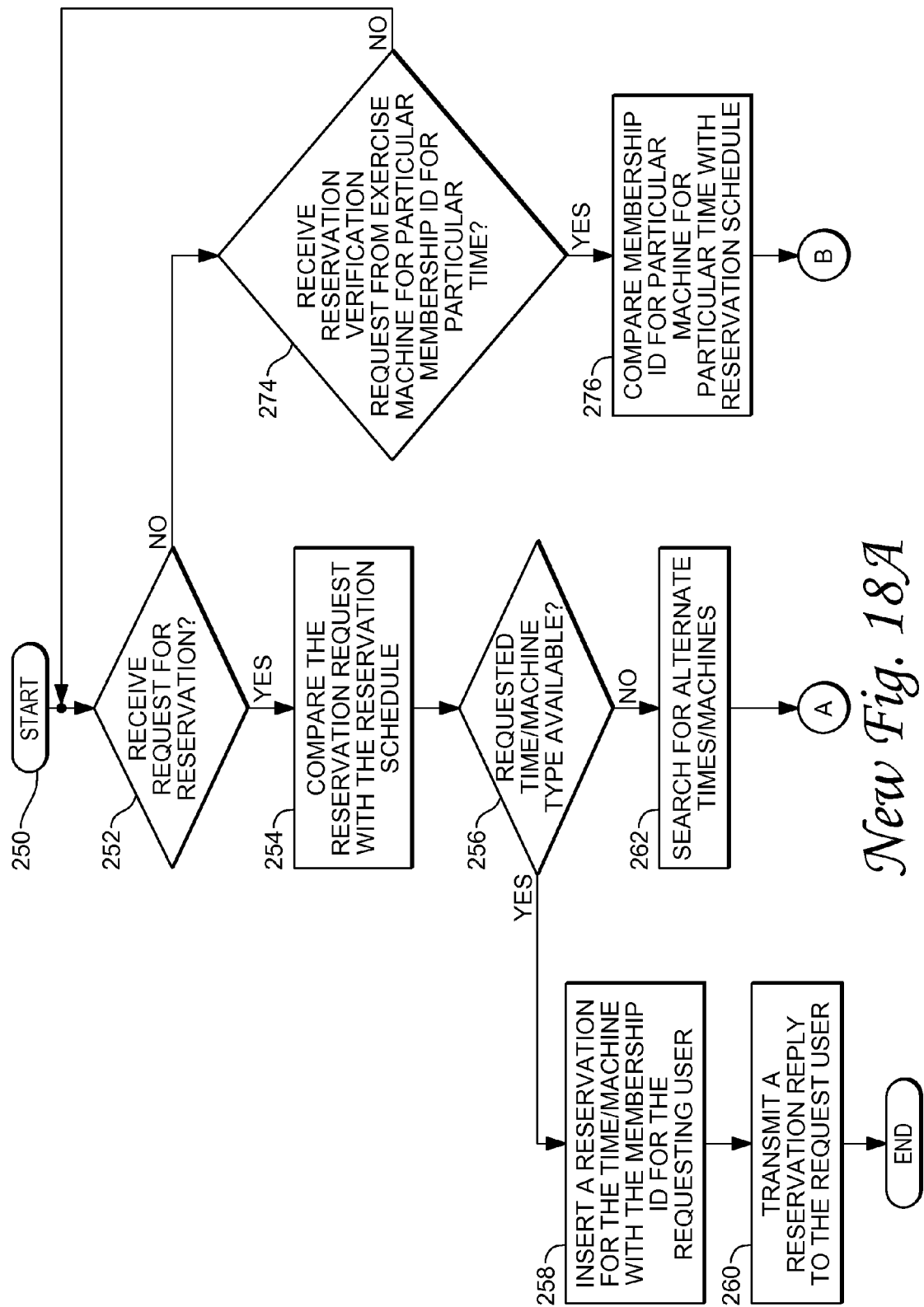

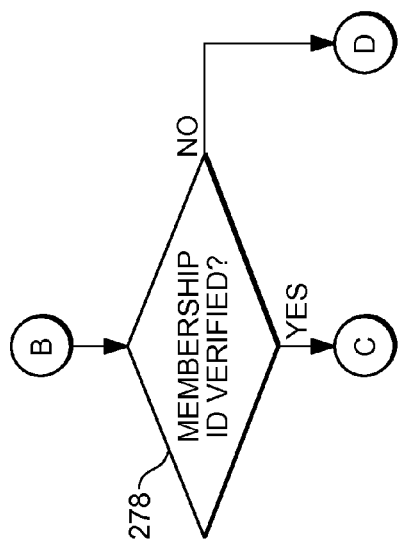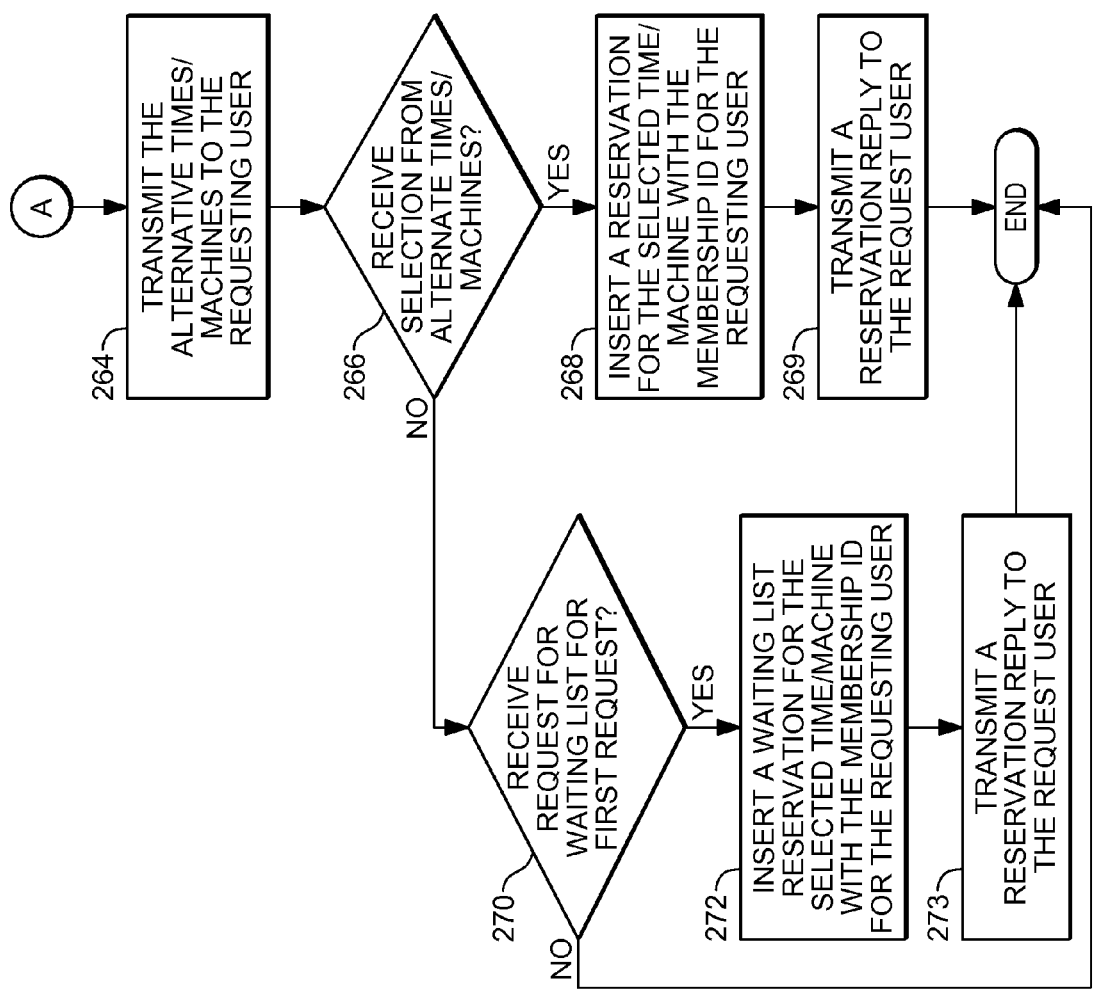
New Fig. 18B

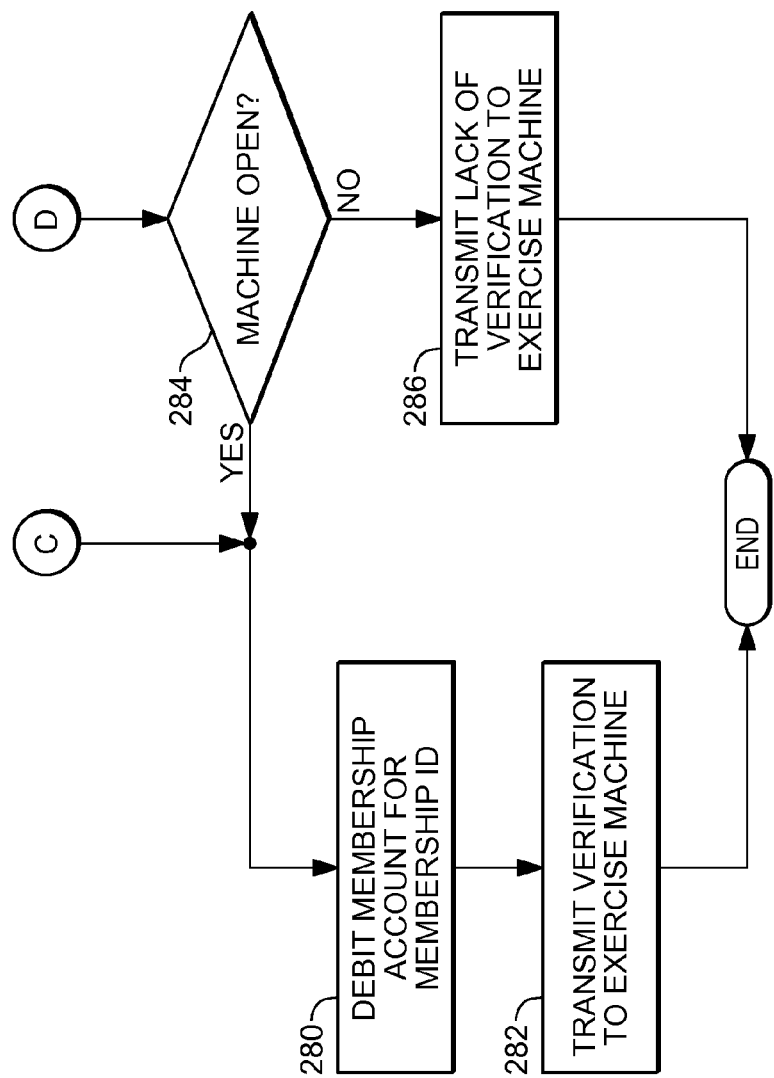

US 6,702,719 C1

EX PARTE
REEXAMINATION CERTIFICATE

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE
SPECIFICATION AFFECTED BY AMENDMENT
ARE PRINTED HEREIN.

Column 1, line 6:

The present application is related to the following co-pending applications, which are filed on even date herewith and incorporated herein by reference:
(1) U.S. patent application Ser. No. 09/561,130
(2) U.S. patent application Ser. No. 09/561,426, *now U.S. Pat. No. 6,601,016 B1*
(3) U.S. patent application Ser. No. 09/561,115, *now U.S. Pat. No. 6,746,371 B1*
(4) U.S. patent application Ser. No. 09/561,134

Column 4, line 7:

FIG. 5 depicts one embodiment of a block diagram of a machine usage system for a health club in accordance with the method, system and program of the present invention; [and]
FIG. 6 illustrates a high level logic flowchart of a process and program for controlling an exercise machine in accordance with the present invention[.];

Column 4, line 13:

*FIG. 7 illustrates a system for utilizing a personal storage device as a personal electronic exercise monitor in accordance with the method, system and program of a preferred embodiment of the present invention;*
*FIG. 8 depicts multiple types of personal storage devices which may be utilized as personal electronic exercise monitors in accordance with the method, system and program of the present invention;*
*FIG. 9 illustrates a block diagram of a reservation system at a health club in accordance with the method, system and program of the present invention;*
*FIGS. 10A-10B illustrate a high level logic flowchart of a process and program for controlling a machine monitor in accordance with the present invention;*
*FIGS. 11A-11B depict a high level logic flowchart of a process and program for utilizing a personal storage device to monitor exercise across multiple diverse exercise machines in accordance with the present invention;*
*FIGS. 12A-12B illustrate a high level logic flowchart of a process and program for specializing a personal storage device in accordance with the present invention;*
*FIG. 13 illustrates a preferred embodiment of a system for utilizing a personal electronic exercise monitor in accordance with the method, system and program of the present invention;*
*FIG. 14 depicts a second embodiment of a system for utilizing a personal electronic exercise monitor in accordance with the method, system and program of the present invention;*
*FIG. 15 illustrates one embodiment of a block diagram of a machine usage system for a health club in accordance with the method, system and program of the present invention;*
*FIG. 16 illustrates a high level logic flowchart of a process and program for controlling an exercise machine in accordance with the present invention;*
*FIGS. 17A-17B depict a high level logic flowchart of a process and program for attaining reservations for a particular user in accordance with the present invention; and*
*FIGS. 18A-18C depict a high level logic flowchart of a process and program for controlling machine usage for a health club in accordance with the present invention.*

Column 5, line 66:

Data exchange across the communications medium is advantageously performed in at least one of multiple available data transmission protocols and is preferably supported by a common data structure format, such as the extensible mark-up language (XML) data structure format. Data transmission protocols may include, but are not limited to, Transmission Control Protocol (TCP), Internet Protocol (IP), Hypertext Transfer Protocol (HTTP), and *the* Bluetooth® *wireless data transmission protocol that communicates data using short-wavelength ultra high frequency (UHF) radio waves in the 2.4 GHz industrial, scientific and medical (ISM) frequency band while the computer system 10 is located local to the exercise machine 38*. In addition, data may be transmitted in a secure manner via encryption or by technologies such as secure socket layer (SSL) or virtual private networks (VPN).

Column 7, line 15:

Multi-machine detectable computer system 10 is advantageously a computer system that is independent of any one exercise machine and is detectable by multiple diverse types of exercise machines. For example, computer system 10 may be a portable computer system, such as a personal digital assistant (PDA), laptop computer system, or mobile telephone system as described in U.S. patent application Ser. No. 09/561,115, *now U.S. Pat. No. 6,746,371 B1,* herein incorporated by reference. In addition, computer system 10 may include a server system that is accessible via a network as described in U.S. patent application Ser. No. 09/561,426, *now U.S. Pat. No. 6,601,016 B1,* herein incorporated by reference. Moreover, portable computer system 10 may comprise a personal storage device, such as a smart card, with limited processing power, where a personal storage device adapter is coupled to exercise machine 38 in order to read the personal storage device, as described in U.S. patent application Ser. No. 09/561,130, herein incorporated by reference.

Column 8, line 56:

For example, at-machine exercise monitor 40 may be temporarily coupled with independent computing devices including, but not limited to, a portable computer system 44, a personal storage device 46 or a remote server system [80] *48* via a communication medium, wherein portable computer system 44, personal storage device 46 or remote server system [80] *48* perform like computer system 10 of FIG. 2.

Column 10, line 59:

Referring now to FIG. 4, there is illustrated a system for monitoring usage of an exercise machine by a manufacturer in accordance with the method, system and program of the present invention. As depicted, exercise machine 38 is connected to network 47 via a communication medium, such that a manufacturer identifier, machine identifier and detected parameters are transmitted to network 47 from exercise machine 38. In this case, the communication medium might utilize a transceiver provided by the manufacturer at an exercise machine, such that the manufacturer incurs any costs related to communicating via network 47. In addition, the transceiver may be equipped with a global positioning system that detects the position of exercise machine 38, *which may be a stationary exercise machine*, such that the location of exercise machine 38 is transmittable. Alternatively, when a customer first initiates use of exercise machine 38, the user may be prompted to enter a location for exercise machine 38 or register a location with the manufacturer.

Column 12, line 9:

With reference now to FIG. 6, there is illustrated a high level logic flowchart of a process and program for controlling an exercise machine in accordance with the present invention. As depicted, the process starts at block 100 and thereafter proceeds to block 102. *Block 102 depicts a determination as to whether or not a personal exercise monitor is selected to control the exercise machine. If a personal exercise monitor is not selected, the process passes to block 106. If a personal exercise monitor is selected, the process passes to block 104.* Block [102] *104* illustrates a determination as to whether or not reservation authorization is received. In order for reservation authorization to be received the user must enter an identifier into a machine monitor or supply the identifier from a personal exercise monitor. If a reservation for the machine has been made, the identifier is compared with an identifier under which the machine is reserved. If there is a match, authorization is provided. Therefore, if authorization is not provided, the process ends. If authorization is provided, the process passes to block [104] *128*. [Block 104 depicts a determination as to whether or not a personal exercise monitor is selected to control the exercise machine. If a personal exercise monitor is not selected, the process passes to block 106. If a personal exercise monitor is selected, the process passes to block 128.]

Column 13, line 28:

With reference now to FIGS. 7-12, the present invention may be executed in a variety of systems, including a variety of computer systems under a number of different operating systems where the system has access to a personal storage device. In a preferred embodiment of the present invention, the computer system is a desktop computer, a network computer, a midrange computer or a mainframe computer. However, in alternate embodiments, the computer system may also be a portable computing system such as a laptop computer, a personal digital assistant, or cellular telephone. In addition, the computer system may be a stand-alone system or part of a network such as a local-area network (LAN) or a wide-area network (WAN). The personal storage device may be a smart card, an ibutton™ microprocessor (ibutton is a trademark of Dallas Semiconductors, Inc.), or other portable storage device that stores data for a particular user or users and is easily transportable. Therefore, in general, the present invention is preferably executed on a computer system that performs computing tasks such as manipulating data from a personal storage device that is accessible to the computer system.

*With reference now to FIG. 7, there is depicted a system for utilizing a personal storage device as a personal electronic exercise monitor in accordance with the method, system and program of a preferred embodiment of the present invention. As depicted, an at-machine exercise monitor 40 for an exercise machine 38 includes a detection system 42x. Preferably, detection system 42x includes real-time monitoring systems such as a pulse monitor, a distance meter, a rate monitor, a time monitor, a strain gauge, an accelerometer and/or any other sensor for measuring the physical activity/performance level of an user on a piece of equipment, as is well known in the art.*

*In addition, machine monitor 40 includes predetermined exercise programs 44x, a fitness calculator 46x, a machine controller 48x, and a monitor usage storage 49. Machine controller 48x transmits signals that control the moving parts of exercise machine 38. A user can select from predetermined exercise programs 44x that control exercise machine 38 or a control program from personal storage device 50x, as will be further described. Predetermined exercise programs 44x preferably simulate particular terrain such as hills or are aimed at achieving a fitness goal such as improving cardiovascular strength. In addition, a user can select a particular level of difficulty for a selected exercise program from predetermined exercise programs 44x.*

*Fitness calculator 46x utilizes monitored data collected by detection system 42x and data about the user (e.g., age, weight) to estimate the number of calories burned and other fitness related statistics. In addition, as will be further described, fitness calculator 46x preferably computes cumulative fitness activity data for a particular user utilizing exercise detected at machine monitor 40 and previous fitness activity and a fitness profile retrieved from personal storage device 50x.*

*Predetermined exercise programs 44x are preferably stored in a data storage structure within data storage medium 41. While in the present embodiment data storage medium 41 is accessible locally by machine monitor 40, in alternate embodiments, data storage medium 41 may be remotely or externally accessible. In addition, machine monitor 40 may be a "dumb" terminal that is controlled by a network computer. Moreover, fitness calculator 46x and predetermined exercise programs 44x may be downloaded onto data storage medium 41 from personal storage device 50x when temporarily provided by a user.*

*Moreover, machine monitor 40 preferably communicates with an input interface 76 and an output interface 78. Input interface 76 may include, but is not limited to including, a keyboard, a mouse, a stylus, a vocal recognition system, a tactile-detectable device, a biometric detection device, a disk drive, and other devices which allow user input to machine monitor 40. Preferably, input interface 76 provides an interface with machine monitor 40 through which a user may supplement data provided by machine monitor 40 and personal storage device 50x. In addition, input interface 76 preferably provides an interface with machine monitor 40 through which a user may customize the functions performed by machine monitor 40 and data stored therein.*

*In accordance with the present invention, machine monitor 40 communicates with a personal storage device I/O adapter 53 via a communications medium. Personal storage device I/O adapter 53 preferably reads from and writes to personal storage device 50x. Personal storage device 50x preferably includes, but is not limited to including, a data storage medium 51, an encryption medium and a processor. The communications medium may utilize wired or wireless communications or other communications media that enables trans-* mission of data to and from personal storage device 50x and machine monitor 40. In addition, the communications medium may include a network, such as the Internet, or a straight data link.

Data exchange across the communications medium is advantageously performed in at least one of multiple available data transmission protocols and is preferably supported by a common data structure format, such as the extensible mark-up language (XML) data structure format. Data transmission protocols may include, but are not limited to, Transmission Control Protocol (TCP), Internet Protocol (IP), Hypertext Transfer Protocol (HTTP), and the Bluetooth® wireless data transmission protocol that communicates data using short-wavelength ultra high frequency (UHF) radio waves in the 2.4 GHz industrial, scientific and medical (ISM) frequency band. In addition, data may be transmitted in a secure manner via encryption or by technologies, such as secure socket layer (SSL) or virtual private networks (VPN).

An example of an XML data file for a control program that might be transmitted from personal storage device 50x to machine monitor 40, as depicted below, preferably contains data that is distinguished by attributes on elements and may be wrapped within a larger element. For example, the data attributed to element "<TimeStamp></TimeStamp>" designates the time that the data was attributed to the XML data file.

<TREADMILL TimeStamp="888965153"

MachineType="Arc2000" UserID=
"JANEXYZ" Speed="30" Elevation="5">

In addition, in an alternate example, the XML data file might be formatted utilizing elements, as illustrated below.

<TimeStamp>888965153</TimeStamp>

<MachineType>Arc2000</MachineType>

<UserID>JANEXYZ</UserID>

<Speed>30</Speed>

<Elevation>5</Elevation>

In the example, as will be further described, machine monitor 40 would receive the example XML data file and utilize the XML data file to control an exercise program operating on exercise machine 38. The above described XML data file example is intended as a functional example of an XML data file that would control the speed and elevation of a treadmill. The elements, format of the elements and data included with the elements is provided to depict an example and is not intended to limit the types of elements, format of elements or data included with elements that are in an XML data file.

In the example of the XML data format as the common transmittable data format, a data validation file such as a document type definition (DTD) or schema is preferably utilized to validate XML data files. In addition, a schema preferably translates multiple XML data files. Moreover, a style sheet such as an extensible stylesheet language (XSL) file is preferably utilized to provide a style specification for the XML data at the receiving system. In particular, DTDs, schemas, and XSL files may be, for example, transmitted with an XML data file to a receiving system or downloaded at the receiving system from an alternate source. In the present example, the DTD or schema would verify that all the data required for transmittal to a particular exercise machine is included in the XML data file. For example, a speed and elevation may be required to validate the XML data file.

Personal storage device 50x preferably acts as a personal electronic exercise monitor that transmits and accesses fitness data across diverse exercise machine platforms. In particular to personal storage device 50x, fitness profile 52x, fitness goals 54x, personal data 56x, control programs 58x and electronic calendar 59x are preferably stored within data storage medium 51 of personal storage device 50x. In the present embodiment, fitness profile 52x, fitness goals 54x, personal data 56x, control programs 58x and electronic calendar 59x are stored on a signal-bearing media embedded within personal storage device 50x. In addition, personal storage device 50x may communicate through a communications medium with other computer systems (not shown) to download data for fitness profile 52x, fitness goals 54x, personal data 56x, control programs 58x and electronic calendar 59x to and from those computer systems. Fitness profile 52x, fitness goals 54x, personal data 56x, control programs 58x, electronic calendar 59x, and other transmittable data stored on personal storage device 50x is preferably efficiently stored in a common transmittable data format, such as XML.

Personal storage device 50x is preferably enabled to store in fitness profile 52x, real-time fitness activity from the cumulative fitness activity data provided from each machine monitor 40. In addition, fitness activity calculated just for an exercise session from each machine monitor 40 may be received and stored. Moreover, exercise indicators, such as pulse rate, distance, speed, etc. may be individually stored in fitness profile 52x from machine monitor 40.

Cumulative fitness activity is preferably computed by each machine monitor 40 by summing previously accumulated fitness activity data retrieved from fitness profile 52x and current fitness activity over a particular time period. In other embodiments, the calculations may be performed in the personal storage device 50x which may have processing capabilities and memory. In summing the previous accumulated fitness activity data and current fitness activity data, machine monitor 40 preferably adjusts the cumulative total as the user exercises to reflect the fitness gained as a result of exercising on multiple machines and according to an individual profile of the user from personal data 56x. The cumulative fitness activity computed at machine monitor 40 is preferably transmitted to personal storage device 50x in real-time. A user can preferably designate the period of time or the selection of exercise machines across which fitness activity data is accumulated. For example, cumulative fitness activity achieved every day or week may be accumulated. Alternatively, cumulative fitness activity for each hour of exercise may be accumulated.

Personal data 56x may include information that is relevant to determining fitness gains in a workout such as weight, height, age, percentage body fat, bone density, metabolism, health problems, and other health related factors. In addition, health data gathered for the user, such as food, liquid and medication intake and environmental exposure may be included. For example, food and liquid intake for a user may be monitored by a personal storage device as described in U.S. Pat. No. 6,859,215 B1 and in U.S. Pat. No. 6,975,910 B1, both herein incorporated by reference. In another example, medication intake for a user may be monitored by a personal storage device as described in U.S. patent application Ser. No. 09/560,993, herein incorporated by reference. Moreover, environmental exposure of a user may be monitored by a personal storage device as described in U.S. Pat. No. 6,622,115 B1, herein incorporated by reference.

In addition, personal data 56x preferably includes a user's output preference for how cumulative fitness activity should be output. For example, a user may prefer a particular font size, colors, output device, graphical application, etc.

Moreover, in personal data 56x, a user can designate multiple levels of security for accessing data stored on personal storage device 50x. For example, particular parts of personal data 56x such as age and bone density may be shielded from transmittal and access without a password. As will be understood by one with ordinary skill in the art, multiple types of security methods and filters may be applied to fitness goals 54x, personal data 56x and other data stored on personal storage device 50x.

In addition, personal data 56x may include an account for a user, such as a debit account, a deductible balance, a credit number, etc. A user's account may be debited in a gym setting, for example, per machine usage, per type of machine utilized, per time on the machine, per number of calories burned or other criteria. Moreover, a user's account may be debited for downloading a particular game or upgrade.

Fitness goals 54x preferably includes data such as target heart rates, target caloric loss, target distance and speed, and other target fitness goals stored in a data storage structure. In addition, fitness goals 54x preferably includes selected exercise sessions. In particular, an exercise program may be pre-selected in fitness goals 54x for a particular exercise machine such that the exercise program is automatically selected if a user selects to utilize that particular exercise machine. An exercise program may include a control program from among control programs 58x or may indicate a selection of a predetermined exercise program from among predetermined exercise programs 44x.

An exercise session may include selections of control programs 58x or of predetermined exercise programs 44x for multiple diverse machines that the user is intended to utilize over a particular period of time. The sessions of control programs 58x may be pre-selected, for example, by the user or a trainer at a computer system and stored as fitness goals 54x. For example, a session may be selected that includes a control program for a 20-minute interval on a rowing machine at a particular seed and thereafter a control program for a 15-minute interval on a step machine with a target heart rate.

In particular, exercise sessions designated by a trainer or computer system in fitness goals 54x may restrict the user to only utilizing a selection of exercise machines according to the designated exercise sessions. Thereby, a trainer or computer may designate a particular exercise session for the user in fitness goals 54x, monitor the user's cumulative fitness activity as a result of performing the exercise sessions from fitness profile 52x and determine if the exercise session needs to be adjusted in order to aid the user in reaching fitness goals. Moreover, in particular, a user may pre-pay to utilize a selection of exercise machines indicated in an exercise session.

Events for an exercise program or session of exercise programs selected in fitness goals 54x may be added to an electronic calendar 59x on personal storage device 50x in order to schedule for the user what type of exercise should be performed each day and how much time should be allotted for exercise.

In addition, machine monitor 40 may include an at-machine trainer application that utilizes fitness profile 52x, fitness goals 54x, and personal data 56x to determine which predetermine exercise programs from among predetermined exercise programs 44x are suitable for the user. A user's personal storage device 50x may be debited for each use of the at-machine trainer application.

Moreover, machine monitor 40 is preferably enabled to transmit predetermined exercise programs 44x to personal storage device 50x such that the predetermined exercise programs are selectable from control programs 58x for setting sessions of control programs in fitness goals 54x. Thereby, if a new exercise machine is available for which control programs 58x does not include a specification, the exercise programs and specifications for the exercise machine can be added to control programs 58x from communication via personal storage device I/O adapter 53 with machine monitor 40. In addition, control programs and machine specifications can preferably be downloaded to control programs 58x from other signal-bearing media such as via the Internet.

Machine monitor 40 is further enable to compare fitness goals 54x with current cumulative fitness data and adjust predetermined exercise programs or control programs in order to aid a user in meeting fitness goals 54x. For example, if a user's target heart rate is 120 beats per minute on a stationary bicycle, however after 10 minutes the user's heart rate is only at 90 beats per minute, the resistance applied to the stationary bicycle may be increased in order to aid the user in increasing the heart beat. In addition, graphical recommendations may be output to the user via output interface 78 in order to meet fitness goals 54x.

Referring still to FIG. 7, a user may utilize personal storage device 50x for varying levels of control of machine monitor 40. For example, for limited control, only the user's filtered personal data may be transmitted from personal storage device 50x to machine monitor 40. By transmitting personal data, the user is relieved from re-entering the same personal data across multiple diverse exercise machine monitors. In another example, for another level of control, the user's personal data and an exercise program selection from among the predetermined exercise programs 44x may be transmitted from personal storage device 50x to machine monitor 40. By transmitting an exercise program selection from among predetermined exercise programs 44x and a difficulty and length of program, an exercise program from predetermined exercise programs 44x is automatically selected and adjusted by machine monitor 40. In another example, for another level of control, a control program may be transmitted from personal storage device 50x to machine monitor 40 that controls machine controller 48x. Thereby, programming of machine monitor 40 is determined by the control program stored on personal storage device 50x.

As previously described, output preferences may be included with personal data 56x on personal storage device 50x. The user-designated output preference may designate output preferences for a particular type of output interface 78 for a particular user. Examples of peripherals include, but are not limited to, a graphical display, an electronic paper, an audio speaker, audio headphones, a tactile detectable device, or a printer. The output preferences may include, but are not limited to, specifications such as the size, type and coloring of a font in a graphical display, the type of tactile-detectable output (e.g., Braille), the language or the metric amount.

In addition, the output preferences may designate a particular game or other program that adds a pictorial representation of a fitness profile. For example, a game that displays the user riding through a jungle forest may be selected. The games and other programs may be stored at machine monitor 40 or personal storage device 50x. Preferably, the user may download games, audio and other programs from signal-bearing media onto personal storage device 50x. Moreover, as will be understood by one with ordinary skill in the art, any output device may perform functions independent of outputting the fitness profile. For example, a user may switch stations, volume and signal bearing media on controllers including, but not limited to, a radio receiver, a television signal receiver, a compact disk player or a tape player that is accessible from exercise machine 38. In addition, as will be understood by one with ordinary skill in the art, any form of visual, auditory or tactile media may be provided for the individual to detect their fitness profile.

It is important to note that a user is able to customize the features available on machine monitor 40. The user may supply input interface 76 or output interface 78. For example, the user may utilize an output interface that includes a color display, or alternatively a black and white display. In addition, for example, the user may download games, audio and other programs from personal storage device 50x into data storage medium 41 of machine monitor 40. Thereby, machine monitor 40 may be continuously upgraded depending on the level of programming provided on personal storage device 50x.

Referring now to FIG. 8, there are illustrated multiple types of personal storage devices which may be utilized as personal electronic exercise monitors in accordance with the method, system and program of the present invention. In the present embodiment, machine monitor 40 includes a display 79, user input interface 76, and a display holder 72. An additional display monitor may be added to display holder 72, preferably a flat screen, electronic paper or liquid crystal display (LCD). Additional display monitors may be controlled by machine monitor 40 or may be controlled independent of machine monitor 40, such as by a network providing cable television. In particular, the user may provide the additional display monitor, or it may be provided by a health club. By offering interchangeable display holder 72, a user may determine the quality of the display monitor utilized for displaying a fitness profile and other graphical images. In addition, although not depicted, additional output devices may be added to exercise machine 38 including, but not limited to, audio speakers, audio headphones, and a tactile detectable tablet.

Multiple types of personal storage devices acting as personal exercise monitors can retrieve data from and transmit data to machine monitor 40 via multiple types of personal storage device I/O adapters. For example, a smart card 64 proffered by a user preferably includes a fitness profile, fitness goals, personal data, control programs, and other additional data that is related and non-related to interaction with machine monitor 40. Machine monitor 40 accesses smart card 64 via a communications medium to a smart card reader 62. As is well known in the art, smart card 64 preferably includes a data storage medium that is enabled for read and write, an encryption medium that encrypts data in the data storage medium and a processor for performing basic functions. In addition, smart card 64 may be controlled by a Java™ virtual machine (JVM) (Java is a trademark of Sun Microsystems, Inc).

In another example, an ibutton 67 included, for example, on a Java ring proffered by a customer and configured to be worn on the body of the customer, such as around an appendage like a finger of the body of the customer, preferably includes a fitness profile, fitness goals, personal data, control programs, and other additional data that is related and non-related to interaction with machine monitor 40. Machine monitor 40 accesses ibutton 67 via a communications medium to an ibutton receptor 65. Currently, an ibutton is an information carrier that typically includes a computer chip that is 16mm or less armored in a stainless steel can. To read/write to ibutton 67, ibutton 67 is detected by ibutton receptor 65, such as a Blue Dot receptor.

Personal storage device 50x is advantageously a personal storage device such as smart card 64 and ibutton 67 that is easily transportable. In addition, personal storage device 50x is customizable to a user's preferences and storage/encryption needs. For example, a user may select a personal storage device with a large storage medium or a small storage medium. In an alternate example, a user may select a personal storage device that transmits data via a contact or via a wireless communication medium. Moreover, personal storage device 50x may include additional applications, such as Java applets that are transmitted to machine monitor 40 and executed therein or are executed on personal storage device 50x. Such applications may provide, for example, a user interface for entering data to be stored in personal data 56x.

Personal storage device I/O adapter 53 may be enabled to read from and write to multiple types of personal storage devices, or only a single type of personal storage device. For example, a smart card reader/writer reads from and writes to smart cards. In another example, an ibutton receptor reads from and writes to a Java ring or other ibutton based personal storage device. However, a reader/writer may combine both functions of the smart card reader/writer and the ibutton receptor. In addition, advantageously, personal storage device readers/writer can detect and transmit wireless transmissions, such as RF transmissions, with the personal storage device. In addition, personal storage device readers/writers can detect and transmit data transmissions through physical contact with the personal storage device.

With reference now to FIG. 9, there is illustrated a block diagram of a reservation system at a health club. A health club server 80 preferably includes a reservation database 81 containing a listing of each exercise machine available and any reservations made for the machines, and user accounts 82. In addition, time limits for each exercise machine may be specified. A user can preferably request reservations for the available exercise machines utilizing a data processing system 83 that is enabled to communicate with health club server 80 via a communications medium, for example, comprising a connection to a server that connects to health club server 80 across network 86. In scheduling reservations, an identifier and/or password for the user is retrieved from personal storage device 50x by data processing system 83 via personal storage device I/O adapter 53 and transmitted and stored with the reservation in reservation database 81. Preferably, a session of scheduled exercise machines is added to an electronic calendar or other scheduling database on personal storage device 50x by data processing system 83. In addition, exercise related data such as an exercise session selection may be transmitted for storage on personal storage device 50x from user entry to data processing system 83 via personal storage device I/O adapter 53.

Health club server 80 preferably tracks statistical data concerning the times utilized and frequency of reservation requests for exercise machines. By tracking reservation data, marketing and financial planning data can be collected. For example, peak hours for a health club can be determined. In addition, by tracking reservation data, a member might be limited in the number of times that they can schedule a reservation and later cancel the reservation.

In addition, health club server 80 may be connected to multiple exercise machine monitors 84a-84n via a communications medium and via personal storage device I/O adapters 82a-82n. Either periodically or in real-time, data from each of exercise machine monitors 84a-84n may be transmitted to health club server 80 in order to track the usage of each exercise machine. In an alternate embodiment, data collected at each of exercise machine monitors 84a-84n may be transmitted periodically or in real-time via a wireless transmission medium to a server or other data storage medium that compiles data about the usage of each exercise machine monitor 84a-84n. Thus, whether an exercise machine is in use in a home gym or a health club, a manufacturer or owner can obtain data about the usage of the exercise machine via communications with each exercise machine monitor 84a-84n.

With reference now to FIGS. 10A-10B, there is illustrated a high level logic flowchart of a process and program for controlling a machine monitor in accordance with the method, system and program of the present invention. As depicted, the process starts at block 100 and thereafter proceeds to block 102. Block 102 illustrates a determination as to whether or not a personal storage device is detected. If a personal storage device is detected, the process passes to block 104. If a personal storage device is not detected, the process passes to block 106.

Block 106 illustrates prompting the user to enter personal data such as age, weight, and height. Thereafter, block 108 depicts prompting the user to select a program, time duration, difficulty and output preference for the program. Next, block 110 illustrates beginning the selected program. Thereafter, block 112 depicts controlling the output of monitored data and any other user-determined output according to the user's output preferences. Block 114 illustrates comparing monitored data with program goals. Next, block 116 depicts a determination as to whether or not the user is meeting the program goals. For example, meeting a program goal might include that a user's heart rate has reached a target level depending on the age and weight of the user. If the user is meeting the program goals, then the process passes to block 120. If the user is not meeting the program goals, then the process passes to block 118.

Block 118 illustrates alerting the user that they are not within the program goals. The user is not within the program goals if the user does not reach the program goals or if the user exceeds the program goals. Next, block 120 depicts computing cumulative fitness activity data with the current monitored data and the fitness profile. Thereafter, block 122 illustrates converting the cumulative fitness activity data into a transmittable data format. Next, block 124 illustrates transmitting the monitored data to the personal storage device. Next, block 126 depicts updating the current output with the monitored data. Thereafter, block 128 depicts a determination as to whether or not the program for the machine is over. If the program is not over, the process passes to block 114. If the program is over, the process passes to block 130. Block 130 illustrates outputting the cumulative fitness activity data from the duration of the exercise program; and the process ends.

Returning to block 104, there is illustrated a determination as to whether or not a reservation authorization is received. A reservation authorization may be received if the machine is available for use and/or a user ID on the personal storage device matches that of a reservation for that machine for that time. If there is not a reservation authorization, then the process ends. If there is a reservation authorization, then the process passes to block 132. Block 132 depicts a determination as to whether personal data and a fitness profile only are received from the personal storage device. If not only personal data and fitness profile are received, the process passes to block 136. If only personal data and fitness profile are received, the process passes to block 134. Block 134 depicts loading the personal data and the fitness profile on the exercise machine monitor; and the process passes to block 108.

Block 136 depicts a determination as to whether or not personal data, a program selection and a fitness profile are received. If personal data, a program selection and a fitness profile are not received, then the process passes to block 140. If personal data, a program selection and a fitness profile are received, then the process passes to block 138. Block 138 illustrates loading the personal data, program selection and fitness profile on the exercise machine monitor; and the process passes to block 110.

Block 140 illustrates a determination as to whether or not a control program and a fitness profile are received. If a control program and fitness profile are not received, the process passes to block 106. If a control program and fitness profile are received, then the process passes to block 142. Block 142 depicts loading the fitness profile and control program on the exercise machine monitor. Thereafter, block 144 illustrates starting the received control program; and the process passes to block 112.

Referring now to FIGS. 11A-11B, there is depicted a high level logic flowchart of a process and program for utilizing a personal storage device to monitor exercise across multiple diverse exercise machines in accordance with the method, system and program of the present invention. As illustrated, the process starts at block 150 and thereafter proceeds to block 152. Block 152 depicts a determination as to whether or not a machine type is detected. In particular, a signal is preferably output from each machine monitor indicating the model and type of exercise machine. If a machine type is not detected, the process passes to block 153. Block 153 illustrates an error; and the process ends. Alternatively, the process may perform a particular number of retries before ending. If a machine type is detected, the process passes to block 154. Block 154 depicts a determination as to whether or not the detected machine is selected in the fitness goals with a predetermined exercise program. If the machine is not included in the fitness goals, then the process ends. If the machine is included in the fitness goals, the process passes to block 156.

Block 156 illustrates a determination as to the control mode selection or data preselected for the machine in the personal storage device. If the control mode is set to transmit personal data, fitness goals and a fitness profile, the process passes to block 162. Block 162 depicts filtering the personal data, fitness goals and fitness profile according to security filters. Next, block 164 illustrates transmitting the filtered data to the machine monitor; and the process passes to block 166. If the control mode is set to transmit personal data and a fitness profile, the process passes to block 158. Block 158 depicts filtering the personal data and fitness profile according to security filters. Next, block 160 illustrates transmitting the filtered data to the machine monitor, and the process passes to block 166. If the control mode is set to transmit a control program, the process passes to block 176. Block 176 depicts transmitting the control program, output preferences, and fitness profile to the machine monitor. Thereafter, the process passes to block 166.

Block 166 depicts a determination as to whether or not cumulative fitness activity data is received. If monitored data is not received, the process iterates at block 166 for a controlled period of time. If monitored data is received, the process passes to block 168. Block 168 illustrates updating the fitness profile. Thereafter, block 170 depicts a determination as to whether or not the program time is over for the machine. If the program time is not over, the process passes to block 166. If the program time is over, the process passes to block 172. Block 172 illustrates a determination as to whether or not the exercise session is over. If the exercise session is over the process ends. If the exercise session is not over, the process passes to block 174. Block 174 depicts transmitting a prompting to the user as to the next exercise machine for the session; and the process ends.

With reference now to FIGS. 12A-12B, there is illustrated a high level logic flowchart of a process and program for specializing a personal storage device in accordance with the method, system and program of the present invention. The process is preferably enabled on a data processing system that is able to transmit data to a personal storage device for a particular user. As depicted, the process starts at block 200 and thereafter proceeds to block 202. Block 202 illustrates a determination as to whether or not a set-up request is made. If a set-up request is made, the process passes to block 204. If a set-up request is not made, the process passes to block 203. Block 203 depicts a determination as to whether or not new session planning is selected. If new session planning is not requested, the process passes to block 202. If new session planning is requested, the process passes to block 216.

Block 204 depicts requesting personal data from the user. Thereafter, block 205 illustrates storing the personal data, preferably in a data storage structure, on the personal storage device. Next, block 206 depicts requesting fitness goals such as race goals, weight loss, cardiovascular strength, etc. Block 207 illustrates storing the fitness goals on the personal storage device. Block 208 depicts requesting a list of exercise machines that are available to the user. The user may download the list of exercise machines to the data processing system, select from a list of pre-loaded exercise machines from the personal storage device, or enter new exercise machines. Thereafter, block 209 illustrates storing the available exercise machines on the personal storage device. Next, block 210 depicts requesting preferred exercise times. Block 212 illustrates storing the preferred exercise times on the personal storage device. Next, block 214 depicts requesting security filter preferences. Block 215 illustrates storing the security filter preferences with the personal data on the personal storage device. Thereafter, block 216 depicts determining an exercise session or sessions. Next, block 218 illustrates displaying the exercise session or sessions; and the process passes to block 220.

Block 220 illustrates filtering the displayed sessions with the user's calendar; and the process passes to block 222. In particular, the user's calendar may be stored on the data processing system or retrieved from the personal storage device. Block 222 depicts detecting user selections of sessions. In addition to the data processing system determining suitable exercise sessions, the user may create their own sessions, or sessions may be downloaded to the data processing system from another source. In addition, a session may include control programs and exercise program selections for a single exercise machine or for multiple exercise machines. Next, block 225 depicts adding the selected sessions to the fitness goals for the user on the personal storage device. Thereafter, block 226 illustrates transmitting a request for reservations for the exercise machines included in the selected sessions. Next, block 228 depicts a determination as to whether or not a reply is received from a reservation server. If a reply is not received, the process passes to block 226. If a reply is received, the process passes to block 230. Block 230 illustrates displaying the reservation listing. Preferably the reservation listing includes exercise machines that have confirmed reservations and alternatives for unavailable machine requests. Block 232 depicts transmitting selections from alternatives. Block 234 illustrates adding the reservations to the user's electronic calendar on the personal storage device; and the process ends.

It is important to note that, although the present invention has been described in the context of a fully functional computer system, those skilled in the art will appreciate that the mechanisms of the present invention are capable of being distributed as a program product in a variety of forms, and that the present invention applies equally regardless of the particular type of signal-bearing media utilized to actually carry out the distribution. Examples of signal-bearing media include, but are not limited to, recordable-type media such as floppy disks or CD-ROMs and transmission-type media such as analogue or digital communications links.

With reference now to FIGS. 13-18, the present invention may be executed in a variety of systems, including a variety of computer systems and electronic devices under a number of different operating systems. In a preferred embodiment of the present invention, the computer system is a portable computing system such as a notebook computer, a palmtop computer, a personal digital assistant, a telephone, or other electronic computing system that may also incorporate communications features that provides for telephony, enhanced telephony, messaging and information services. However, the computer system may also be, for example, a desktop computer, a network computer, a midrange computer or a mainframe computer. Preferably, in order to enable at least one of these communications features, the computer system is able to be connected to a network, such as the Internet by either a wired link or wireless link. In addition, the computer system may be a stand-alone system or part of a network such as a local-area network (LAN) or a wide-area network (WAN). Therefore, in general, the present invention is preferably executed in a computer system that performs computing tasks such as manipulating data in a storage that is accessible to the computer system. In addition, the computer system includes at least one output device and at least one input device.

With reference now to FIG. 13, there is depicted one embodiment of a block diagram of a system for utilizing a personal electronic exercise monitor in accordance with the method, system and program of the present invention. As depicted, computer system 10 preferably acts as a personal electronic exercise monitor that accesses, interprets, and controls fitness data across diverse exercise machine platforms. A fitness profile 52x, fitness goals 54x, personal data 56x, control programs 58x, and electronic calendar 59x are preferably stored within a data storage medium 51 of computer system 10. While in the present embodiment data storage medium 51 is depicted as internally accessible to computer system 10, in alternate embodiments, data storage medium 51 may be externally or remotely accessible to computer system 10. In addition, the data stored in data storage medium 51 is preferably updatable through downloads to computer system 10. Moreover, the data stored on computer system 10 is preferably efficiently stored in a particular data transmission format, such as extensible mark-up language (XML), or is easily convertible into the data transmission format.

Computer system 10 preferably communicates with multiple diverse exercise machines, such as exercise machine 38, via a bi-directional communications medium (or across a communication interface). In addition, as will be further described, computer system 10 may communicate with alternate server systems via a bi-directional communication medium. The communications medium may include wired or wireless communications or other communications media that enables bi-directional transmission of data. Moreover, the communications medium may include a link to a network, such as the Internet, or a direct data link.

In a wired embodiment of the communications medium, for example, exercise machine 38 is connected to computer system 10 via parallel, serial, or USB ports, or the communication adapter as depicted in FIG. 1. In a wireless embodiment of the communications medium, for example, exercise machine 38 is wirelessly connected to computer system 10 via infrared, radio frequency (RF), cellular and other wireless transmissions which are detected by computer system 10.

Data exchange across the communications medium is advantageously performed in at least one of multiple available data transmission protocols and is preferably supported by a common data structure format, such as the extensible mark-up language (XML) data format. Data transmission protocols may include, but are not limited to, TCP/IP, HTTP, TFP, CDMA, and the Bluetooth® wireless data transmission protocol that communicates data using short-wavelength ultra high frequency (UHF) radio waves in the 2.4 GHz industrial, scientific and medical (ISM) frequency band. In addition, data may be transmitted in a secure manner via encryption or by technologies, such as secure socket layer (SSL) or virtual private networks (VPN).

An example of an XML data file that might be transmitted from computer system 10 to exercise machine 38, as depicted below, preferably contains data that is distinguished by attributes on elements and may be wrapped within a larger element. For example, the data attributed to element "<TimeStamp></TimeStamp>" designates the time that the data was attributed to the XML data file.

```
<TREADMILL TimeStamp="888965153" MachineType=
    "Arc2000" UserID="JANEXYZ"

Speed="30" Elevation="5">
```

In addition, in an alternate example, the XML data file might be formatted utilizing elements, as illustrated below.

```
<TimeStamp>888965153</TimeStamp>

<MachineType>Arc2000</MachineType>

<UserID>JANEXYZ</UserID>

<Speed>30</Speed>

<Elevation>5</Elevation>
```

In the example, as will be further described, exercise machine 38 would receive the example XML data file and utilize the XML data file to control operation of exercise machine 38. The above described XML data file example is intended as a functional example of an XML data file that would control the speed and elevation of a treadmill. The elements, format of the elements and data included with the elements is provided to depict an example and is not intended to limit the types of elements, format of elements or data included with elements that are in an XML data file.

In the example of the XML data format as the common transmittable data format, a data validation file such as a document type definition (DTD) or schema is preferably utilized to validate XML data files. In addition, a schema preferably translates multiple XML data files. Moreover, a style sheet such as an extensible style sheet language (XSL) file is preferably utilized to provide a style specification for the XML data at the receiving system. In particular, DTDs, schemas, and XSL files may be, for example, transmitted with an XML data file to a receiving system or downloaded at the receiving system from an alternate source. In the present example, the DTD or schema would verify that all the data required for transmittal to a particular exercise machine is included in the XML data file. For example, a speed and elevation may be required to validate the XML data file.

Exercise machine 38 advantageously transmits measurements in the common transmittable data structure format from real-time monitoring systems associated with exercise machine 38 including, but not limited to a pulse monitor, a distance meter, a rate monitor, a time monitor, a strain gauge, an accelerometer and/or any other sensor for measuring the physical activity/performance level of a user on a piece of equipment.

Detected exercise signals, such as a pulse, distance, rate, time, strain, etc., are preferably transmitted from exercise machine 38 in a common transmittable data format. For example, an example of an XML data file for a pulse monitor is described below where a user's pulse is measured between a particular time period at 80 beats per minute. In addition, an alternate form of XML formatting may be utilized.

```
<TimeRange>888965153,888965160</TimeRange>

<MachineID>45365</MachineID>

<MachineType>PulseMonitor</MachineType>

<Rate>80</Rate>
```

Computer system 10 is preferably enabled to compute current fitness activity based on the detected exercise in the form of a pulse, distance, rate, time, strain, acceleration, and any other sensed value that may be utilized to compute current fitness activity. In addition, in calculating current fitness activity, factors such as previously accumulated fitness activity stored in fitness profile 52x, personal data 56x, and the type of exercise machine are utilized to compute a realistic fitness assessment. Thereby, computer system 10 is enabled to compute and store cumulative real-time fitness activity within fitness profile 52x over a selected time period or session from across multiple diverse exercise machines. Cumulative fitness activity over a selected time period is preferably computed from summing previously accumulated fitness activity for the selected time period with the current fitness activity. In summing the previously accumulated fitness activity and current fitness activity, computer system 10 may adjust the cumulative total to more closely reflect the fitness gained as a result of exercising on multiple machines over a period of time. For example, if a user exercises for an hour across three different exercise machines, the amount of calories burned by the user actually increases with prolonged exercise over a particular amount of time determined for that user and therefore is adjusted in the cumulative fitness activity.

In addition, to storing cumulative real-time fitness activity for a user over a particular period of time, individual sessions of fitness activity may also be recorded. For example, if a user exercises on a treadmill for twenty minutes and a rowing machine for 20 minutes, a cumulative fitness profile may be calculated and stored in fitness profile 52x. In addition, fitness activity achieved from exercise on the treadmill and rowing machine may be stored as separate exercise sessions. Moreover, in addition to calculating cumulative fitness activity according to previously accumulated fitness activity, personal data 56x and the type of exercise machine, the types of food eaten by the user that day, fluid intake, medication usage and environmental exposure may be utilized to determine cumulative fitness activity data.

In particular, in addition to receiving detected exercise signals from exercise machine 38, detected exercise may be input by a user via input interface 66 or from another monitoring device. For example, a user may count the number of jumping jacks that they perform during a break between utilizing exercise machines. The number of jumping jacks can be entered into computer system 10 via an input interface 66 and computer system 10 computes fitness activity data for the jumping jacks and updates the cumulative real-time fitness activity data. Input interface 66 may include, but is not limited to including, a keyboard, a mouse, a stylus, a vocal recognition system, a tactile-detectable device, a biometric detection device, a disk drive, a personal storage device adapter, and other devices which allow user input to computer system 10. Preferably, input interface 66 provides an interface with computer system 10 through which a user may supplement data provided by exercise machine 38. In addition, input interface 66 preferably provides an interface with computer system 10 through which a user may customize the functions performed by computer system 10 and data stored therein.

In addition, in an alternate embodiment, the real-time exercise monitoring systems may be associated with computer system 10. For example, a pulse monitor may be associated with computer system 10 that detects the pulse of a user as the user exercises on exercise machine 38, independent of exercise machine 38. In another example, a pulse rate monitor may record a pulse rate for a user over a period of time, such as during a foot race, and transmit the recorded exercise signals to computer system 10, independent of an exercise machine. Therefore, an exercise machine need not include monitoring systems for detecting health parameters during exercise. In addition, the cumulative fitness activity data calculated at computer system 10 may be supplemented with exercise measurements taken for exercise performed independent of exercise machine 38.

Personal data 56x stored at computer system 10 may include information that is relevant to determining fitness gains in a workout such as weight, height, age, percentage body fat, bone density, metabolism, health problems, prescriptions, diet, and other health related factors. For example, food and liquid intake for a user may be monitored by a portable computer system. In another example, medication intake for a user may be monitored by a portable computer system. Moreover, environmental exposure of a user may be monitored by a portable computer system.

In addition, personal data 56x preferably includes a user's output preference for how cumulative fitness activity should be output. For example, a user may prefer a particular font size, colors, output device, graphical application, etc.

Moreover, in personal data 56x, an individual can designate multiple levels of security for accessing fitness profile 52x, fitness goals 54x and personal data 56x stored on computer system 10. For example, particular parts of personal data 56x such as age and bone density may be shielded from transmittal and access without a password. As will be understood by one with ordinary skill in the art, multiple types of security methods and filters may be applied to fitness goals 54x, personal data 56x and other data stored on computer system 10.

Fitness goals 54x preferably includes data such as target heart rates, target caloric loss, target distance and speed, and other target fitness goals stored in a data storage structure. In addition, fitness goals 54x preferably includes selections of control programs from control programs 58x for particular exercise machines and selected exercise sessions. In particular, a control program may be preselected in fitness goals 54x for a particular exercise machine such that the control program is automatically selected if a user selects to utilize that particular exercise machine. In addition, parameters for the control program, such as a level of difficulty, may also be included in fitness goals 54x.

An exercise session may include multiple selections of control programs from among control programs 58x for multiple machines that the user is intended to utilize over a particular period of time. The session of selections of control programs may be pre-selected by the user, determined by a trainer, or selected by computer system 10 dependent upon the goals of the user and other factors. For example, a session may be selected that includes a control program for a 20-minute interval on a rowing machine at a particular speed and thereafter a control program for a 15-minute interval on a step machine with a target heart rate. Moreover, as will be further described, exercise sessions may include selections of predetermined control programs on an at-machine exercise monitor.

A control program selection or session of control program selections in fitness goals 54x may be added to an electronic calendar 59x on computer system 10 in order to schedule for the user what type of exercise should be performed each day and how much time should be allotted for exercise. This function is particularly helpful for people wanting to follow a particular workout schedule. For example, athletes training for an event, such as a triathlon, where a schedule is imperative to reach fitness goals and where multiple diverse exercise modes are performed consecutively, would benefit from an exercise program stored on electronic calendar 59x. In addition, a trainer may prescribe a particular workout schedule for a client on electronic calendar 59x.

As mentioned previously, if a user or trainer does not select exercise sessions for an individual, computer system 10 may provide suitable exercise sessions that are selectable by the individual or a trainer. In particular, computer system 10 is preferably enabled to determine sessions based on an individual's personal data 56x, exercise machines available to the user, and other fitness goals provided such as the type of event training for, the date of the event and other pertinent data.

Alternatively, fitness goals may include weight loss, cardiovascular strengthening, muscle strengthening, etc. Preferably, an individual can enter or download specific types of exercise machines that are available in a personal gym or health club.

Control programs 58x preferably includes multiple control programs for controlling each of multiple types of diverse exercise machines. For example, for a treadmill, one control program may provide for a flat race while another control program may provide for a hill workout. Each of control programs 58x preferably designate a particular type of work out session with goals for reaching particular speeds, heights, heart rates, etc. dependent upon personal data 56x. In particular, control programs 58x are preferably downloadable onto computer system 10.

The parameters of control programs 58x are advantageously adjustable by the user such that the intensity of each control program may be varied. For example, a user may select to utilize a particular control program, such as a hill workout, for thirty minutes one day and for forty-five minutes another day. Computer system 10 is preferably enabled to adjust the hill workout control program for varying times, difficulties, etc.

When computer system 10 connects to exercise machine 38, computer system 10 preferably detects the type of exercise machine from a machine type signal transmitted from exercise machine 38 in the common transmittable data structure format. In response to detecting the type of exercise machine, computer system 10 checks whether a control program for the detected exercise machine is designated in fitness goals 54x. If a control program is not preselected, then a selection of control programs available for controlling the machine are displayed to the user via output interface 68. In response to a pre-selection of a control program or a current designation of a control program, with parameter selections, a machine control signal is transmitted from computer system 10 to exercise machine 38 in order to control the functions of exercise machine 38.

As a user exercises, the detected exercise signals received from exercise machine 38 are preferably compared with the goals of the exercise program. For example, a heart rate of the user may be compared with a target heart rate for the control program in view of personal data 56x or a current cumulative fitness activity level in fitness profile 52x. If a user is not reaching target goals, an indicator may be output to the user via output interface 68 and/or the machine control signal to exercise machine 38 adjusted to facilitate the user reaching target goals. If the user is exceeding target goals, an indicator may be output to the user via output interface 68 and/or the machine control signal adjusted to reduce exercise intensity.

As another feature of computer system 10, a user may compete against other users via a communications medium with other computer systems that are monitoring real-time fitness activity data, where the fitness activity data is transmittable in the common data structure format. For example, alternate computer system 59 is monitoring real-time fitness activity data on alternate exercise machine 61. In particular, multiple users may be utilizing the same type of exercise machine or diverse types of exercise machines where a single type of display profile or multiple types of display profiles show each of the user's paces compared with the other users. For example, one user may be riding a stationary bicycle while another user is running on a treadmill. A graphically rendered game may be displayed to each of the users at each of the user's computer systems that are monitoring their exercise. The game or other application preferably compensates for the differences in types of exercise to show one user's position compared to another user's position in the game. The users may be within an area local to one another, such as in a gym, or may be within a global area and are connected via a network connection.

As previously described, output preferences may be included with personal data 56x on computer system 10. The user-designated output preference may designate output preferences for a particular type of output interface 68 for a particular user. Output interface 68 may include, but is not limited to including, a graphical display, an electronic paper, an audio speaker, audio headphones, a tactile detectable device, or a printer. The output preferences may include, but are not limited to specifications such as the size, type and coloring of a font in a graphical display, the type of tactile-detectable output (e.g., Braille), the language or the metric amount displayed.

In addition, the output preferences may designate a particular game or other program that adds a pictorial representation of a fitness profile. For example, a game that displays the user riding through a jungle forest may be selected. Moreover, as will be understood by one with ordinary skill in the art, any output device may perform functions independent of outputting the fitness profile. For example, a user may switch stations, volume and signal bearing media on controllers including, but not limited to, a radio receiver, a television signal receiver, a compact disk player or a tape player that is accessible from exercise machine 38. In addition, as will be understood by one with ordinary skill in the art, any form of visual, auditory or tactile media may be provided for the individual to detect their fitness profile.

Computer system 10 is advantageously a portable computer system, such as a digital telephone, a personal digital assistant, a laptop computer, or a palmtop computer that is easily transportable and compact. In addition, computer system 10 is advantageously utilized as a personal exercise monitor for monitoring exercise across multiple diverse exercise machine platforms and a temporary controller for controlling movement of multiple diverse exercise machine platforms when in use by a user associated with computer system 10. It is important to note that a user is able to customize the features available on computer system 10. Since the user advantageously supplies computer system 10, the user may select the type and quality of desired output. For example, the user may download games, audio and other programs from signal-bearing media into data storage medium 51. In addition, the user may utilize a computer system that includes a color display, or alternatively a black and white display. In addition, it is important to note that computer system 10 may be continuously upgraded without requiring the upgrade of machine monitor 40.

In addition, it is important to note that the exercise machine monitoring system of the present invention may provide for a gym setting in which a user's account included in personal data 56x is charged as the user exercises and the user provides computer system 10 in order to control each of multiple diverse exercise machines. For example, a user's account may be debited per machine usage, per type of machine utilized, per time on the machine, per number of calories burned or other criteria. Moreover, a user's account may be debited for downloading a particular game or upgrade.

With reference now to FIG. 14, there is depicted a second embodiment of a system for utilizing a personal electronic exercise monitor in accordance with the method, system and program of the present invention. As depicted, an exercise machine includes an at-machine exercise monitor 40 that includes a fitness calculator 46x, predetermined exercise programs 44x, and a machine controller 48x within a data storage medium 41 accessible to at-machine exercise monitor 40. At-machine exercise monitor 40 also includes an input interface 76 and an output interface 78.

At-machine exercise monitor 40 preferably enables a user to control exercise machine 38 both independently of computer system 10 and dependent upon computer system 10. Input interface 76 provides an interface for a user to enter personal data and select a predetermined exercise program from among predetermined exercise programs 44x. Fitness calculator 46x calculates current fitness activity based on personal data and detected exercise signals. Machine controller 48x transmits a control signal to exercise machine 38 for controlling movement of exercise machine 38.

Alternatively, personal data may be transmitted from computer system 10 to at-machine exercise monitor 40. In addition, alternatively, a selection of a predetermined exercise program may be transmitted to at-machine exercise monitor 40. Moreover, alternatively, at-machine exercise monitor 40 acts as a "dumb terminal" receiving a control signal from computer system 10, such that exercise machine 38 is completely controlled by computer system 10.

Personal data transmitted from computer system 10 to at-machine exercise monitor 40 is preferably transmitted in an XML data file as shown below, where at-machine exercise monitor 40 is enabled to read the data file. In addition, a predetermined exercise program selection of program "5"

for thirty minutes at exercise level "8" may be included in the data file. Moreover, an alternate form of XML formatting may be utilized.

<TimeStamp>888965153</TimeStamp>

<UserID>GeorgeG</UserID>

<Age>30</Age>

<Weight>180</Weight>

<Program>5</Program>

<ProgramTime>003000</ProgramTime>

<ProgramLevel>8</ProgramLevel>

Referring now to FIG. 15, there is illustrated a block diagram of a machine usage system for a health club in accordance with the method, system and program of the present invention. Computer system 10 is preferably enabled to transmit a schedule request for particular exercise machines during a particular time period in the common transmittable data structure format via a network connection such as the Internet or a LAN connected to a health club server 80. The schedule request may come from a predetermined schedule of exercise events or from a user request for a particular machine during a particular time period. For example, an XML data file including a request for a "Tread505" exercise machine on February 23, 2000 from 1 PM to 1:30 PM is depicted below. In addition, an alternate form of XML formatting may be utilized.

<TimeStamp>888965153</TimeStamp>

<UserID>GeorgeG</UserID>

<MachineRequest>Tread505</MachineRequest>

<MachineRequestDay>02.23.2000</MachineRequestDay>

<MachineReqTime>13:00:00,13:30:00</MachineReqTime>

Health club server 80 preferably includes a reservation database 81 containing a listing of each exercise machine available and any reservations made for the machines. In addition, time limits for each exercise machine may be specified.

Moreover, a maximum holding period for each machine may be identified. For example, a particular machine that is in high demand may require that a user is present at the machine within five minutes of a reservation time. If a user is not present at a machine within the maximum holding period, health club server 80 may transmit an indicator to the next user on a waiting list indicating that the machine is available or allow a user already present at the machine to begin exercising.

In addition, health club server 80 preferably includes user accounts 82 that may include a prepaid debit amount, a credit card number, bank account number, or other financial information that can be utilized to charge a user for a particular service.

Associated with each of user accounts 82 may include health restrictions for each user that the health club has been notified of by the user. For example, if the user has notified the health club of a heart condition then the user account may include information about the user's heart condition. Advantageously, the health club may restrict a user from making reservations for or receiving authorization for use of any exercise machine that may conflict with any health restrictions for the user.

The health club server 80 compares the schedule requests from computer system 10 with available time slots in reservation database 81 and transmits a list of available scheduling to computer system 10. When the exact time slot requested by the user is not available, health club server 80 advantageously provides available times for machines that are similar in aerobic purposes to the machine requested and/or times that are available for the requested machine within a particular range of the requested times.

The individual may then select to reserve exercise machines from the available scheduling. In scheduling time, an identifier and/or password for the user is transmitted and stored with the reservation, such as the user's account id. In addition, the individual may select to be placed on a waiting list for exercise machines that are currently reserved during a requested time period. Computer system 10 is then notified if the time slot opens. Preferably, a session of scheduled exercise machines is added to and/or verified in an electronic calendar or other scheduling database on computer system 10.

In addition, health club server 80 may be connected to multiple at-machine exercise machines 84a-84n via a communications medium. Exercise machines 84a-84n communicate with computer system 10 to receive a reservation identifier for the user and transmit verification requests to health club server 80 to verify that a user has a reservation for an exercise monitor being requested by that user. In verifying a user, both the reservation stored in reservation database 81 and the account information for the user stored in user accounts 82 are verified. In addition, the user account may be debited. In receiving a verification, exercise machines 84a-84n are enabled to function for the verified user.

In receiving a reservation identifier at exercise machines 84a-84n, the reservation identifier may be received from computer system 10. In addition, the reservation identifier may be received from other forms of data storage, such as a personal storage device proffered by the user at exercise machines 84a-84n. Moreover, a user may manually input a reservation identifier at an input interface of exercise machines 84a-84n.

For a machine that is not in use, a user may enter an account number at the machine and receive a schedule of how long the machine will be available. For example, during non-peak hours at a health club, making reservations for a machine is not as imperative. However, if a user that does not have a reservation requests to utilize a machine, health club server 80 preferably transmits a length of time for which the exercise machine may be utilized until the next reservation or for a time limit assigned to that exercise machine according to reservations database 81. Thereby, users without previous reservations may utilize an exercise machine.

Health club server 80 preferably tracks statistical data concerning the times utilized and frequency of reservation requests for exercise machines. By tracking reservation data, marketing and financial planning data can be collected. For example, peak hours for a health club can be determined. In addition, by tracking reservation data, a member might be limited in the number of times that they can schedule a reservation and later cancel the reservation. Either periodically or in real-time, data from each of exercise machines 84a-84n may be transmitted to health club server 80 in order to track the usage of each exercise machine. In an alternate embodiment, data collected at each of exercise machines 84a-84n may be transmitted periodically or in real-time via a wireless transmission medium to a server or other data storage medium that compiles data about the usage of each exercise machines 84a-84n. Thus, whether an exercise machine is in use in a home gym or a health club, a manufacturer or owner can obtain data about the usage of the exercise machine via communications with each exercise machines 84a-84n.

Advantageously, according to the present invention, a particular user may be a member at multiple health clubs that charge according to machine usage. If the user is unable to reserve an exercise machine for a particular time at one health club, the user may query other health clubs to make a reservation for the particular machine for the particular time.

With reference now to FIG. 16, there is illustrated a high level logic flowchart of a process and program for controlling an exercise machine in accordance with the present invention. As depicted, the process starts at block 100 and thereafter proceeds to block 102. Block 102 illustrates a determination as to whether or not a user account entry is detected at the exercise machine. If an identifier for a user or a user account is not received at the exercise machine, then the process iterates at block 102. If an identifier for a user or user account is received at the exercise machine, then the process passes to block 104.

Block 104 depicts transmitting the user account to the reservation server for the exercise machine for authorization. Next, block 106 illustrates a determination as to whether or not a reservation authorization is returned. If a reservation authorization is not returned, then the process ends. If a reservation authorization is returned, then the process passes to block 108. Block 108 depicts a determination as to whether or not a control program is received. If a control program is not received, then the process ends. If a control program is received, then the process passes to block 110. Block 110 illustrates beginning the received control program and the process ends.

Referring now to FIGS. 17A-17B, there is illustrated a high level logic flowchart of a process and program for attaining reservations for a particular user in accordance with the present invention. As depicted the process starts at block 200 and thereafter proceeds to block 202. Block 202 illustrates a determination as to whether or not a request for scheduling according to the user's fitness goals is received. If a request for scheduling is not received, then the process passes to block 208. If a request for scheduling is received, then the process passes to block 204.

Block 204 depicts adding exercise events to a user's schedule according to fitness goals and schedule availability. Next, block 206 illustrates transmitting a request for reservations for prescheduled exercise events to a reservation server; and the process passes to block 212.

Block 208 illustrates a determination as to whether or not a request for reservation scheduling is received. In particular, a request for reservation scheduling may be entered by a user independent of fitness goals and other criteria utilized by the computer system to determine scheduling. If a request for reservation scheduling is not received, then the process passes to block 202. If a request for reservation scheduling is received, then the process passes to block 210. Block 210 depicts transmitting a request for reservations for a particular exercise machine for a particular time range to a reservation server; and the process passes to block 212.

Block 212 depicts a determination as to whether or not a listing of reservation availability is received. If a listing of availability is not received, then the process ends. If a listing of availability is received, then the process passes to block 214. Block 214 illustrates displaying the reservation list; and the process passes to block 216.

Block 216 illustrates a determination as to whether or not a user selection is received from the reservation listing. If a user selection is not received from the reservation listing, then the process ends. If a user selection is received from the reservation listing, then the process passes to block 218. Block 218 depicts transmitting the listing selection to the reservation server; and the process passes to block 220.

Block 220 depicts a determination as to whether or not a reservation confirmation is received. If a reservation confirmation is not received, then the process ends. If a reservation confirmation is received, then the process passes to block 222. Block 222 illustrates confirming the reservation in the user schedule and the process ends.

With reference now to FIGS. 18A-18C, there is depicted a high level logic flowchart of a process and program for controlling machine usage for a health club in accordance with the present invention. As depicted, the process starts at block 250, and thereafter proceeds to block 252. Block 252 depicts a determination as to whether or not a request for a reservation is received. If a request for a reservation is not received, then the process passes to block 274. If a request for a reservation is received, then the process passes to block 254. Block 254 illustrates comparing the reservation request with the reservation schedule at the health club server. Next, block 256 depicts a determination as to whether or not the requested machine type and time are available. If the requested machine type and time are not available, then the process passes to block 262. If the requested machine type and time are available, then the process passes to block 258. Block 258 illustrates inserting a reservation for the machine type and time in the reservation schedule with the membership id of the requesting user. Next, block 260 depicts transmitting a reservation reply to the computer system for the requesting user; and the process ends.

Block 262 depicts searching the reservation schedule for alternative times and machine types. Next, block 264 illustrates transmitting the alternative times and machine types of the computer system for the requesting user. Thereafter, block 266 depicts a determination as to whether or not a selection from among the alternatives is received at the health club server from the computer system for the requesting user. If a selection from among the alternatives is received, then the process passes to block 268. Block 268 illustrates inserting a reservation for the selected machine type and time in the reservation schedule with the membership id of the requesting user. Next, block 269 depicts transmitting a reservation reply to the computer system for the requesting user; and the process ends.

Returning to block 266, if a selection from among the alternatives is not received, then the process passes to block 270. Block 270 depicts a determination as to whether or not a request for the waiting list for the user's first machine type and time request is received. If a request for the waiting list is not received, then the process ends. If a request for the waiting list is received, then the process passes to block 272. Block 272 illustrates inserting a waiting list reservation for the machine type and time in the reservation schedule with the membership id of the requesting user. Next, block 273 depicts transmitting a reservation reply to the computer system for the requesting user; and the process ends.

Block 274 illustrates a determination as to whether or not a reservation verification request is received from a particular exercise machine for a particular membership id for a particular time. If a reservation verification request is not received, then the process passes to block 252. If a reservation verification request is received, then the process passes to block 276. Block 276 depicts comparing the membership id with the particular exercise machine and time in the reservation schedule. Next, block 278 illustrates a determination as to whether or not the membership id is verified in the reservation schedule. If the membership id is not verified, then the process passes to block 284. If the membership id is verified, then the process passes to block 280.

Block 280 illustrates debiting the membership account for the membership id. The membership account may be debited according to the type of exercise machine, the length of reservation for the exercise machine or other criteria. Next, block 282 depicts transmitting a verification to the requesting exercise machine; and the process ends.

Block 284 depicts a determination as to whether or not the requested machine has an open reservation. The reservation system may determine that if a user has not arrived at a machine after 5 minutes from a reservation time for the machine, then the machine is opened for the next individual on the waiting list or for a person at the machine requesting usage. If the machine does not have an open reservation, then the process passes to block 286, which depicts transmitting a lack of verification to the requesting exercise machine, then the process ends. If the machine does have an open reservation, then the process passes to block 280.

It is important to note that, although the present invention has been described in the context of a fully functional computer system, those skilled in the art will appreciate that the mechanisms of the present invention are capable of being distributed as a program product in a variety of forms, and that the present invention applies equally regardless of the particular type of signal-bearing media utilized to actually carry out the distribution. Examples of signal-bearing media include, but are not limited to, recordable-type media such as floppy disks or CD-ROMs and transmission-type media such as analogue or digital communications links.

THE DRAWINGS FIGURE HAVE BEEN
CHANGED AS FOLLOWS:

New FIGS. 7-18C have been added.

AS A RESULT OF REEXAMINATION, IT HAS BEEN DETERMINED THAT:

Claims 1-14 are cancelled.

New claims 15-69 are added and determined to be patentable.

15. The method as recited in claim 1, wherein:
the exercise machine is a first exercise machine;
the independent computing device is portable;
the exercise-related data is received wirelessly from the independent computing device while the independent computing device is located local to the first exercise machine; and
the exercise-related data includes a data file that specifies control parameters of, or specifies a selection of, a particular exercise control program configured to control the first exercise machine.

16. The method as recited in claim 15, wherein:
the independent computing device is connected to the Internet over a wireless communications medium.

17. The method as recited in claim 16, wherein:
the independent computing device is a laptop computer.

18. The method as recited in claim 16, wherein:
the independent computing device is a notebook computer.

19. The method as recited in claim 16, wherein:
the independent computing device is a palmtop computer.

20. The method as recited in claim 16, wherein:
the independent computing device is a personal digital assistant.

21. The method as recited in claim 16, wherein:
the independent computing device is a portable computing device that includes telephony communication features and messaging communication features.

22. The method as recited in claim 21, wherein:
the independent computing device is a mobile telephone.

23. The method as recited in claim 16, wherein:
the independent computing device is a personal storage device.

24. The method as recited in claim 23, wherein:
the independent computing device is a wireless smart card.

25. The method as recited in claim 15, wherein:
the independent computing device is configured to be worn around an appendage of the body of the particular user.

26. The method as recited in claim 15, further comprising:
prompting the particular user, using the independent computing device, to proceed from the first exercise machine to a second exercise machine in order to continue an exercise session on the second exercise machine.

27. The method as recited in claim 15, wherein:
the exercise-related data for the particular user includes output preferences.

28. The method as recited in claim 27, wherein:
the output preferences include audio output preferences.

29. The method as recited in claim 27, wherein:
the output preferences include visual output preferences.

30. The method as recited in claim 27, wherein:
the output preferences include an output preference for a game.

31. The method as recited in claim 27, wherein:
the output preferences include an output preference specifying a particular font type.

32. The method as recited in claim 27, wherein:
the output preferences include an output preference specifying a particular font color.

33. The method as recited in claim 27, wherein:
the output preferences include an output preference specifying a particular font size.

34. The method as recited in claim 27, wherein:
the output preferences include an output preference specifying a particular type of output device.

35. The method as recited in claim 27, wherein:
the output preferences include an output preference specifying a particular language.

36. The method as recited in claim 15, wherein:
the receiving of the exercise-related data is accomplished wirelessly using a data transmission protocol that uses short-wavelength ultra high frequency (UHF) radio waves in the 2.4 GHz industrial, scientific and medical (ISM) frequency band.

37. The method as recited in claim 15, wherein:
the exercise-related data includes a schedule of the first exercise machine and of a second exercise machine for the particular user to utilize.

38. The method as recited in claim 15, further comprising:
wirelessly sending, from the first exercise machine to the independent computing device, a first indicator of detected fitness activity performed by the particular user on the first exercise machine;
wirelessly sending, from a second exercise machine to the independent computing device, a second indicator of detected fitness activity performed by the particular user on the second exercise machine; and calculating, using the independent computing device, cumulative fitness activity performed by the particular user on the first exercise machine and on the second exercise machine using the first indicator and the second indicator.

39. The method as recited in claim 38, further comprising:

receiving, at the independent computing device, manual input entered by the particular user specifying fitness activity that was performed by the particular user independent of any exercise machine; and calculating, using the independent computing device, cumulative fitness activity performed by the particular user on the first exercise machine, on the second exercise machine, and independent of any exercise machine.

40. The method as recited in claim 15, wherein:
the exercise-related data for the particular user includes financial account data of the particular user.

41. The method as recited in claim 40, further comprising:
debiting a financial account corresponding to the financial account data of the particular user based on usage of the first exercise machine by the particular user and based on usage of a second exercise machine by the particular user.

42. The method as recited in claim 15, wherein:
the exercise-related data for the particular user includes a fitness goal of the particular user.

43. The method as recited in claim 42, further comprising:
wirelessly sending, from the first exercise machine to the independent computing device, an indicator of detected fitness activity performed by the particular user on the first exercise machine;

comparing, using the independent computing device, the indicator of the detected fitness activity to the fitness goal of the particular user; and presenting, on an output device of the independent computing device, an indication that the particular user is not meeting the fitness goal of the particular user or is exceeding the fitness goal of the particular user.

44. The method as recited in claim 15, wherein:
the independent computing device is detectable by the first exercise machine via a wireless communication medium.

45. The method as recited in claim 15, wherein:
the exercise-related data for the particular user includes food intake data of the particular user as monitored by the independent computing device.

46. The method as recited in claim 15, wherein:
the exercise-related data for the particular user includes liquid intake data of the particular user as monitored by the independent computing device.

47. The method as recited in claim 15, wherein:
the exercise-related data for the particular user includes medication intake data of the particular user as monitored by the independent computing device.

48. The method as recited in claim 15, wherein:
the exercise-related data for the particular user includes environmental exposure data of the particular user as monitored by the independent computing device.

49. The method as recited in claim 15, wherein:
the receiving of the exercise-related data is accomplished using an infrared wireless transmission.

50. The method as recited in claim 15, wherein:
the receiving of the exercise-related data is accomplished using a radio frequency (RF) wireless transmission.

51. The method as recited in claim 15, wherein:
the receiving of the exercise-related data is accomplished using a cellular wireless transmission.

52. The method as recited in claim 15, wherein:
the exercise-related data is received at the first exercise machine in extensible mark-up language (XML) data structure format.

53. The method as recited in claim 15, wherein:
the receiving of the exercise-related data is accomplished using data encryption.

54. The method as recited in claim 15, wherein:
the first exercise machine is a treadmill; and
the data file specifies speed for the treadmill and specifies elevation for the treadmill.

55. The method as recited in claim 15, wherein:
the independent computing device includes an input interface.

56. The method as recited in claim 55, wherein:
the input interface of the independent computing device includes a keyboard.

57. The method as recited in claim 55, wherein:
the input interface of the independent computing device includes a stylus input device.

58. The method as recited in claim 55, wherein:
the input interface of the independent computing device includes a vocal recognition input system.

59. The method as recited in claim 55, wherein:
the input interface of the independent computing device includes a tactile-detectable input device.

60. The method as recited in claim 55, wherein:
the input interface of the independent computing device includes a biometric detection input device.

61. The method as recited in claim 15, wherein:
an output interface of the independent computing device includes a graphical display.

62. The method as recited in claim 15, wherein:
an output interface of the independent computing device includes an electronic paper.

63. The method as recited in claim 15, wherein:
an output interface of the independent computing device includes an audio speaker.

64. The method as recited in claim 15, wherein:
an output interface of the independent computing device includes a tactile detectable output device.

65. The method as recited in claim 15, wherein:
an output interface of the independent computing device includes a printer.

66. The method as recited in claim 15, wherein:
the control parameters of the particular exercise control program are included in the data file.

67. The method as recited in claim 1, wherein:
the exercise machine is a stationary exercise machine configured to guide the particular user in controlled exercise movements and includes a global positioning system (GPS) that detects a physical location of the stationary exercise machine inside of a building;

the method further comprises tracking usage of the stationary exercise machine at each of multiple physical locations within the building; and the method further comprises comparing location-dependent usage rates.

68. The method as recited in claim 67, further comprising:
transmitting, from a remote server to the stationary exercise machine, a software update over the Internet.

69. The method as recited in claim 67, further comprising:
transmitting, from a remote server to the stationary exercise machine, a game application over the Internet.

* * * * *